United States Patent [19]

Tang

[11] Patent Number: 5,760,066
[45] Date of Patent: Jun. 2, 1998

[54] COMPOUNDS AND METHODS FOR INHIBITING HYPER-PROLIFERATIVE CELL GROWTH

[75] Inventor: Peng Cho Tang, Moraga, Calif.

[73] Assignee: Sugen, Inc., Redwood City, Calif.

[21] Appl. No.: 634,917

[22] Filed: Apr. 19, 1996

Related U.S. Application Data

[63] Continuation-in-part of Ser. No. 426,789, Apr. 21, 1995.

[51] Int. Cl.$^6$ .................. A01N 43/80; C07D 413/12
[52] U.S. Cl. .................................. 514/378; 548/248
[58] Field of Search .................... 548/248; 514/378

[56] References Cited

U.S. PATENT DOCUMENTS

| | | |
|---|---|---|
| 4,087,535 | 5/1978 | Heubach et al. . |
| 4,284,786 | 8/1981 | Kammerer et al. . |
| 4,351,841 | 9/1982 | Kammerer et al. . |
| 4,992,271 | 2/1991 | Fernandez et al. . |
| 5,217,999 | 6/1993 | Levitzki et al. . |
| 5,268,382 | 12/1993 | Bartlett et al. . |
| 5,314,685 | 5/1994 | Tyle et al. . |
| 5,476,866 | 12/1995 | Kuo et al. . |
| 5,506,249 | 4/1996 | Kuo et al. . |

FOREIGN PATENT DOCUMENTS

| | | |
|---|---|---|
| 3101093 | 1/1993 | Australia . |
| 0013376 | 12/1979 | European Pat. Off. . |
| 0413329 | 2/1991 | European Pat. Off. . |
| 0520722 | 6/1992 | European Pat. Off. . |
| 0551230 | 7/1993 | European Pat. Off. . |
| 0607775 | 7/1994 | European Pat. Off. . |
| 0607776 | 7/1994 | European Pat. Off. . |
| 0607777 | 7/1994 | European Pat. Off. . |
| 0646578 | 9/1994 | European Pat. Off. . |
| 2240104 | 7/1991 | United Kingdom . |
| 9117748 | 11/1991 | WIPO . |
| 9221641 | 4/1992 | WIPO . |
| 9220642 | 11/1992 | WIPO . |
| 9519169 | 7/1995 | WIPO . |
| 9524190 | 9/1995 | WIPO . |

OTHER PUBLICATIONS

Borisevich et al., "Reactions of arylamides of a α-[(phenylamino)methylidene]-β-oxo(thiono)butyric acid with hydroxylamine and substituted hydrazines," *Chemical Abstracts* 107(7):726 at abstract No. 58919a (1987).

Sjogren et al., "Synthesis and Biological Activity of a Series of Diaryl–Substituted α–Cyano–β–hydroxypropenamides, a New Class of Anthelmintic Agents," *J. Med. Chem.* 34:3295–3301 (1991).

Andrews et al. (American Veterinary Medicine Association Panel on Euthanasia), "1993 Report of the AVMA Panel on Authanasia," *J. American Veterinary Medicine Association* 202(2):229–249 (1993).

Axton et al., "Novel Immunosuppressive Butenamides," *J. Chem. Soc. Perkin Trans.* pp. 2203–2213 (1992).

Bartlett et al., "Leflunomide (HWA 486), a novel immunomodulating compound for the treatment of autoimmune disorders and reactions leading to transplantation rejection," *Agents and Actions* 32:10–21 (1991).

Bartlett et al., "Effects of leflunomide on immune responses and models of inflammation," *Springer Semin. Immunopathol.* 14:381–394 (1993).

Baselga et al., "Antitumor Effects of Doxorubicin in Combination With Anti–epidermal Growth Factor Receptor Monoclonal Antibodies," *J. of Natl. Cancer Institute* 85(16):1327–1333 (1993).

(List continued on next page.)

Primary Examiner—Johann Richter
Assistant Examiner—Ebenezer Sackey
Attorney, Agent, or Firm—Lyon & Lyon LLP

[57] ABSTRACT

Compounds and methods for inhibiting hyper-proliferative cell growth. The compounds and method are preferably used to treat patients having a hyper-proliferative cell disorder.

28 Claims, 4 Drawing Sheets

OTHER PUBLICATIONS

Baudy et al., "Potent Quinoxaline–Spaced Phosphono α–Amino Acids of the AP–6 Type as Competitive NMDA Antagonists: Synthesis and Biological Evaluation," *J. Med. Chem.* 36:331–342 (1993).

Bilder et al., "Tyrphostins inhibit PDGF–induced DNA synthesis and associated early events in smooth muscle cells," *Am. J. Physiol.* 260(Cell Physiol.29):C721–C730 (1991).

Birchall et al., "Compositions for killing internal parasites containing 3–teri–alkyl–4–hydroxy–5–halobenzylidene–malononitriles," *Chemical Abstracts* 88:535 (1978).

Bryckaert et al., "Inhibition of Platelet–Derived Growth Factor–Induced Mitogenesis and Tyrosine Kinase Activity in Cultured Bone Marrow Fibroblasts by Tyrphostins," *Exp. Cell Research* 199:255–261 (1992).

Bustelo and Barbacid, "Tyrosine Phosphorylation of the vav Proto–Incogene Product in Activated B Cells," *Science* 256:1196–1199 (1992).

Caraglia et al., "Cytosine arabinoside increases the binding of $^{125}$I–labelled epidermal growth factor and $^{125}$I–transferrin and enhances the in vitro targeting of human tumour cells with anti–(growth factor receptor)mAb," *Cancer Immunol. Immunother.* 37:150–156 (1993).

*Cecil Textbook of Medicine*, eds. Wyngaarden, Smith, Bennett, W.B. Saunders (1992) p. 2220.

Chen and Okayama, "Calcium Phosphate–Mediated Gene Transfer: A Highly Efficient Transfection System for Stably Transforming Cells with Plasmid DNA," *BioTech.* 6:632–638 (1988).

Cherwinski et al., "The Immunosuppressant Leflunomide Inhibits Lymphocyte Progression Through Cell Cycle by a Novel Mechanism," *J. Pharmacology and Exp. Therap.* 272:460–468 (1995).

Chong et al., "Leflunomide, a Novel Immunosuppressive Agent," *Transplantation* 55:1361–1366 (1993).

Chong et al., "Leflunomide, a Novel Immunomodulatory Agent: In Vitro Analyses of the Mechanism of Immunosupression," *Transplant. Proc.* 25:747–749 (1993).

Conn et al., "Purification of a glycoprotein vascular endothelial cell mitogen from a rat glimo–derived cell line," *Proc. Natl. Acad. Sci. USA* 87:1323–1327 (1990).

Decker and Lohmann–Matthes, "A quick and simple method for the quantitation of lactate dehydrogenase release in measurements of cellular cytotoxicity and tumor necrosis factor (TNF) activity," *J. Immunol. Methods* 115:61–69 (1988).

Ehrlich and Bogert, "Experiments in the Veratole and Quinoxaline Groups," *J. Org. Chem.* 12:522 (1947).

Ferris et al., "Synthesis of Zuinazoline Nucleosides from Ribose and Anthranilonitrile. Application of Phase–Transfer Catalysis in Nucleoside Synthesis," *J. Org. Chem.* 44(2):173–178 (1979).

Fry et al., "New insights into protein–tyrosine kinase receptor signaling complexes," *Protein Science* 2:1785–1797 (1993).

Gazit et al., "Tyrphostins. 1. Synthesis and Biological Activity of Protein Tyrosine Kinase Inhibitors," *J. Med. Chem.* 32:2344–2352 (1989).

Gazit et al., "Tyrphostins. 2. Heterocyclic and α–Substituted Benzylidenemalononitrile Tyrphostins as Potent Inhibitors of EGF Receptor and ErbB2/neu Tyrosine Kinases," *J. Med. Chem.* 34:1896–1907 (1991).

Gazit et al., "Tyrphostins. 3. Structure–Activity Relationship Studies of a α–Substituted Benzylidenemalononitrile 5–S–Aryltyrphostins" *J. Med. Chem.* 36:3556–3564 (1993).

Glant et al., "Immunodulation of proteoglycan–induced progressive polyarthritis by leflunomide," *Immunopharmacology* 23:105–116 (1992).

Gottardis et al., "Estradiol–Stimulated Growth of MCF–7 Tumors Implanted in Athymic Mice: A Model to Study the Tumoristatic Action of Tamoxifen, " *J. Steroid Biochem.* 30(1–6):311–314 (1988).

Gulbins et al., "Tyrosine Kinase–Stimulated Guanine Nucleotide Exchange Activity of Vav in T Cell Activation," *Science* 260:822–825 (1993).

Hale et al., "Prognastic value epidermal growth factor receptor expression in cervical carcinoma," *J. Clin. Pathol.* 46:149–153 (1993).

Hambelton and Mahon, "Drug actions on delayed–type hypersensitivity in rats with developing and established adjuvant arthritis," *Agents and Actions* 29:328–332 (1990).

Harris et al., "Breast Cancer (First of Three Parts)," *New England J. of Medicine* 327(5):319–328 (1992).

Heldin, "Structural and functional studies on platelet–derived growth factor," *EMBO Journal* 11:4251–4259 (1992).

Hoekstra et al., "Differential effects of steurosporine and tyrphostins on receptor tyrosine kinase autophosphorylation and peptide substrate phosphorylation," *Experimental Therapeutics* from 84th Annual Meeting of American Association for Cancer Research, vol. 34, #2455 (1993).

Honegger et al., "Point Mutation at the ATP Binding Site of EGF Receptor Abolishes Protein–Tyrosine Kinase Activity and Alters Cellular Routing," *Cell* 5:199–209 (1987).

Houck et al., "The Vascular Endothelial Growth Factor Family: Identification of a Fourth Molecular Species and Characterization of Alternative Splicing of RNA," *Molecular Endocrinology* 5:1806–1814 (1991).

Issidorides and Haddadin, "Benzofurazan Oxide. II. Reactions with Enolate Anions," *J. Org. Chem.* 31:4067–4068 (1966).

Ju et al., "Leflunomide inhibits cytokine–induced DNA synthesis of rabbit synovial cells in culture," *Zhongguo Yaoli Xuebao* 15:223–226 (1994).

Ju et al., "Leflunomide inhibits PAF induced DNA synthesis in rabbit synovial cells in PAF production from rat peritomeal macrophages," *Yaoxue Xuebao* 92:90–94 (1994).

Karameris et al., "Expression of Epidermal Growth Factor (EGF) and Epidermal Growth Factor Receptor (EGFR) in Gastric and Colorectal Carcinomas. An Immunohistological Study of 63 Cases," *Path. Res. Pract.* 189:133–137 (1993).

Koenders et al., "Epidermal growth factor receptor and prognosis in human breast cancer: a prospective study," *Breast Cancer Research and Treatment* 25:21–27 (1993).

Korzeniewski and Callewaert, "An Enzyme–Release Assay for Natural Cytotoxicity[1]," *J. Immunol. Methods* 64:313 (1983).

Kuechle et al., "Prevention of Kidney and Skin Graft Rejection in Rats by Leflunomide, a New Immunodulating Agent," *Transplant Proc.* 23:1083–1806 (1991).

Lee and Salemnick, "Purine N–Oxides, LXII. 2,4Dioxopyrido[2,3–d]pyrimidine N–Oxides," *J. Org. Chem.* 40(24):3608–3610 (1975).

Levitzki, "Tyrphostins—Potential Antiproliferative Agents and Novel Molecular Tools," *Biochem. Pharm.* 40(5):913–918 (1990).

Ley and Seng, "Synthesen unter Verwendung von Benzofuroxan," *Synthesis* 1975:415–422 (1975).

Lyall et al., "Tyrphostins Inhibit Epidermal Growth Factor (EGF)–Receptor Tyrosine Kinase Activity in Living Cells and EGF–stimulated Cell Proliferation," *J. Bio. Chem.*, 264:14503–14509 (1989).

Marshall, E., "Search for a Killer: Focus Shifts from Fat to Hormones," *Science* 259:618–621 (1993).

Mattar et al., "Inhibition of the epidermal growth factor receptor tyrosine kinase activity by leflunomide," *FEBS Letters* 2:161–164 (1993).

Mattar et al., "Inhibition of the epidermal growth factor receptor tyrosine kinase activity by leflunomide," *FEBS Letters* vol. 334:161–164 (1993) [19].

McChesney et al., "An Evaluation of Leflunomide in the Canine Renal Transplantation Model," *Transplantation* 57:1717–1722 (1994).

Millauer et al., "High Affinity VEGF Binding and Developmental Expression Suggest Flk–1 as a Major Regulator of Vasculogenesis and Angiogenesis," *Cell* 72:835–846 (1993).

Mosmann, "Rapid Colorimetric Assay for Cellular Growth and Survival: Application to Proliferation and Cytotoxicity Assays," *J. Immunol. Methods* 65:55–63 (1983).

Muller et al., "BCR First Exon Sequences Specifically Activate the BCR/ABL Tyrosine Kinase Oncogene of Philadelphia Chromosome–Positive Human Leukemias," *Mol. Cell. Biol.* 11:1785–1792 (1991).

Nichterlein et al., "Leflunomide (HWA 486) Prolongs Course of Murine Listeriosis," *Immnuol. Infect. Dis.* 4:18–22 (19949).

Ogawa et al., "Therapeutic Effects of Leflunomide, a New Antirheumatic Drug, on Glomerulonephritis Induced by the Antibasement Membrane Antibody in Rats," *Clin Immunol. Immunopath.* 61:103–118 (1991).

Ohmichi et al., "The Tyrosine Kinase Inhibitor Tyrphostin Blocks the Cellular Actions of Nerve Growth Factor," *Biochemistry* 32:4650–4658 (1993).

Ogawa et al., "Effects of leflunomide on glomerulonephritis induced by antibasement membrane antibody in rats," *Agents Actions* 31:321–328 (1990).

Osborne et al., "Effect of Estrogens and Antiestrogens on Growth of Human Breast Cancer Cells in Athymic Nude Mice," *Cancer Research* 45:584–590 (1985).

Osherov et al., "Selective Inhibition of the EGF and Neu receptors by Tyrophostins," *J. Cell Biochem.* S17A:237 (1993).

Ozzello and Sordat, "Behavior of Tumors Produced by Transplantation of Human Mammary Cell Lines in Athymic Nude Mice," *Eur. J. Cancer* 16:553–559 (1980).

Patterson et al., "3–Carboxy–5–methyl–N–[4–(trifluoromethyl)phenyl]–4–isoxazolecarboxamide, a New Prodrug for the Antiarthritic Agent 2–Cyano–3–hydroxy–N–[4–(trifluoromethyl)phenyl]–2–butenamide," *J. Med. Chem.* 35:507–510 (1992).

Peterson and Barnes, "Genistein and Biochanin A Inhibit the Growth of Human Prostate Cancer Cells but not Epidermal Growth Factor Receptor Tyrosine Autophosphorylation," *The Prostate* 22:335–345 (1993).

Pigott et al., "Expression of epidermal growth factor receptor in human glioblastoma multiforme," *Brit. J. of Neurosurgery* 7:261–265 (1993).

Plate et al., "Vascular endothelial growth factor is a potential tumour angiogenesis factor in human glimoas in vivo," *Nature* 359:845–848 (1992).

Plate et al., "Up–Regulation of Vascular Endotheial Growth Factor and Its Cognate Receptors in a Rat Glimoa Model of Tumor Angiogenesis," *Cancer Research* 53:5822–5827 (1993).

Plate et al., "Platelet–Derived Growth Factor Receptor–$\beta$ is Induced during Tumor Development and Upregulated during Tumor Progression in Endothelial Cells in Human Gliomas," *Laboratory Investigation* 4:529–534 (1992).

Pollack et al., "Response of malignant glioma cell lines to epidermal growth factor and platelet–derived growth factor in a serum–free medium," *J. Neurosurg.* 73:106–112 (1990).

Ren et al., "Identification of a Ten–Amino Acid Proline–Rich SH3 Binding Site," *Science* 259:1157–1161 (1993).

Rendu et al., "Inhibition of Platelet Activation by Tyrosine Kinase Inhibitors," *Biochem. Pharm.* 44(5):881–888 (1992).

Rosenthal et al., "Conditioned Medium from Mouse Sarcoma 180 Cells Contains Vascular Endothelial Growth Factor," *Growth Factors* 4:53–59 (1990).

Ross et al. "The pathogenesis of atherosclerosis: a perspective for the 1990's ," *Nature* 362:801–809 (1993).

Rusch et al., "Differential Expression of the Epidermal Growth Factor Receptor and Its Lgands in Primary Non–Small Cell Lung Cancers and Adjacent Benign Lung," *Cancer Research* 53:2379–2385 (1993).

Rygaard and Povlsen, "Heterotransplantation of a Human Malignant Tumour to 'Nude' Mice," *Acta path. microbiol. scand.* 77:758–760 (1969).

Schorlemmer et al., "Prolongation of Allogeneic Transplantated Skin Grafts and Induction of Tolerance by Leflunomide, a New Immunosuppresive Isoxazol Derivative," *Transplant. Proc.* 25:763–767 (1993).

Schornagel et al., "Synthesis and Evaluation of 2,4–Diaminoquinazoline Antifolates with Activity Against Methotrexate–Resistant Human Tumor Cells," *Biochem. Pharm.* 33(20):3251–3255 (1984).

Scott et al., "p185$^{HER2}$ Signal Transduction in Breast Cancer Cells, " *J. Bio. Chem.* 266(22):14300–14305 (1991).

Seibert et al., "Clonal Variation of MCF–7 Breast Cancer Cells in Vitro and in Athymic Nude Mice," *Cancer Research* 43:2223–2239 (1983).

Shafie and Grantham, "Role of Hormones in Growth and Regression of Human Breast Cancer Cells (MCF–7) Transplanted into Athymic Nude Mice," *J. Natl Cancer Institute* 67(1):51–56 (1981).

Shweiki et al., "Vascular endothelial growth factor induced by hypoxia may mediate hypoxia–initiated angiogenesis," *Nature* 359:843–845 (1992).

Skehan et al., "New Colorimetric Cytotoxicity Assay for Anticancer–Drug Screening," *J. Natl. Cancer Inst.* 82:1107–1112 (1990).

Talmadge and Twardzik. "Role of Cytokines in Inflammation and Autoimmunity," *Agents and Actions* 35S:135–141 (1991).

Thoenes et al., "Leflunomide (HWA 486) Inhibits Experimental Autoimmune Tubulointerstitial Nephritis in Rats," *Int. J. Immunopharmacol.* 11:921–929 (1989).

Ueno et al., "Inhibition of PDGF $\beta$ Receptor Signal Transduction by Coexpression of a Truncated Receptor," *Science* 252:844–252 (1991).

Ulrichs et al., "Suppression of Natural Xenophile Antibodies With the Novel Immunomodulating Drug Leflunomide," *Transplant Proc.* 24:718–719 (1992).

Wada et al., "Anti–receptor antibodies reverse the phenotype of cells transformed by two interacting proto–oncogene encoded receptor proteins," *Oncogene* 5:489–495 (1990).

Waltenberger et al., "Different Signal Transduction Properties of KDR and Flt1, Two Receptors for Vascular Endothelial Growth Factor," *J. Biol. Chem.* 269:26988–26995 (1994).

Warri et al., "Estrogen Suppression of erbB2 Expression is Associated with Increased Growth Rate of ZR-75-I Human Breast Cancer Cells In Vitro and in Nude Mice," *Int. J. Cancer* 49:616–623 (1991).

Weithmann et al., "Effect of leflunomide on constitutive and inducible pathways of cellular eicosanoid generation," *Agents Actions* 41:164–170 (1994).

Williams et al., "Immunosuppressive Effects of Leflunomide in a Cardiac Allograft Model," *Transplantation Proc.* 25:745–746 (1993).

Williams et al., "Leflunomide in Experimental Transplantation," *Transplantation* 57:1223–1231 (1994).

Xiao et al., "Effect of Leflunomide in Control of Acute Rejection in Hamster-to-Rat Cardiac Xenografts," *Transplantation Proceedings* 26:1263–1265 1994).

Xiao et al., "Leflunomide Controls Rejection in Hamster to Rat Cardiac Xenografts," *Transplantation* 58:828–834 (1994).

Yaish et al., "Blocking of EGF-Dependent Cell Proliferation by EGF Receptor Kinase Inhibitors," *Science* 242:933–935 (1988).

Yoneda et al., "The Antiproliferative Effects of Tyrosine Kinase Inhibitors Tyrphostins on a Human Squamous Cell Carcinoma in Vitro and in Nude Mice," *Cancer Research* 51:4430–4435 (1991).

Zeillinger et al., "EGF-R and Steroid Receptors in Breast Cancer: A Comparison with Tumor Grading, Tumor Size, Lymph Node Involvement, and Agen," *Clin. Biochem.* 26:221–227 (1993)Andrews et al. (American Veterinary Medicine Association Panel on Euthanasia), 1993 Report of the AVMA Panel on Euthanasia *J. American Veterinary Medicine Association* 202(2):229–249 (1993).

Zielinski et al., "Effects of leflunomide (HWA 486) on expression of lymphocyte activation markers," *Agents Actions* 38:(Special Conference Issue) C80–C82 (1993).

Dati et al., "Inhibition of c–erbB–2 oncogene expression by estrogens in human breast cancer cells," *Oncogene* 5:1001–1006 (1990).

Floege et al., "Factors involved in the regulation of mesangial cell proliferation in vitro and in vivo," *Kidney International* 43:S47–S54 (1993).

Osherov et al., "Selective Inhibition of the Epidermal Growth Factor and HER2/Neu Receptors by Tyrphostins," *Journal of biological Chemistry* 268:11134–11142 (1993).

Rudorf and Augustin, "Alkylierungs–Und Arylierungsreaktionen Mit eminalen Dithiolaten," *Phosphorus and Sulfer* 9:329–336 (1981).

Borisevich et al., "Reactions of arylamides of α [(phenylamino) methylidene] β oxo(thiono)butyric acid with hydroxylamine and substituted hydrazines," *Ukr. Khim. Zh.* 52(6):641 647 (1986).

Kunzek et al., "Oxydationreaktionen von α cyan thioacetanilid," *Zeitschrift Fur Chemi* 15(4):145 146 (1975).

5,760,066

COMPOUNDS AND METHODS FOR INHIBITING HYPER-PROLIFERATIVE CELL GROWTH

RELATED APPLICATIONS

The present application is a continuation-in-part of Tang U.S. Ser. No. 08/426,789, filed Apr. 21, 1995, which is hereby incorporated by reference herein in its entirety, including the drawings.

FIELD OF THE INVENTION

The present invention concerns compounds and methods for inhibiting hyper-proliferative cell growth.

BACKGROUND OF THE INVENTION

The citation of art provided in the present application is not an admission that the art is prior art to the claimed invention.

Hyper-proliferative cell growth contributes to different disorders such as autoimmune associated disorders, atherosclerosis, and cancers. The compounds leflunomide (also known as 5-methylisoxazole-4 carboxylic acid-(4-trifluromethyl)-anilide) and N-(4-trifluoro-methylphenyl)-2-cyano-3-hydroxycrotonamide have been said to be useful in inhibiting hyper-proliferative cell growth. Leflunomide acts as a prodrug for the in vivo formation of N-(4-trifluoro-methylphenyl)-2-cyano-3-hydroxycrotonamide.

According to the abstracts of Kömmerer F-J, et al., U.S. Pat. No. 4,284,786 (1981) and Kömmerer F-J, et al., U.S. Pat. No. 4,351,841 (1982), leflunomide:

has antirheumatic, antiphlogistic, antipyretic and analgesic action, and can be used for the treatment of multiple sclerosis.

Heubach, U.S. Pat. No. 4,087,535 (1978) indicates that leflunomide has anti-inflammatory and analgetic properties.

Robertson S. M. and Lang L. S., European Patent Application 0 413 329 A2 (published 1991) which is concerned with 5-methylisoxazole-4-carboxylic acids that encompass leflunomide, asserts:

The present invention is directed to methods for treating ocular diseases with immune etiology through the use of 5-methyl-isoxazole-4-carboxylic acid anilides and hydroxyethlidene-cyano acetic acid anilide derivatives. In addition the compounds are useful for treating ocular manifestation associated with systemic diseases with immune etiology. The compounds exhibit immunosuppressive, antiinflammatory, and mild antiallergic activity and are useful for the treatment of eye diseases such as uveitis (including rheumatoid nodules), retinitis, allergy (vernal keratocon junctivitis and allergic or giant papillar conjunctivitis) and dry eye (Sjogren's syndrome). Additionally the compounds are useful for prolonging graft survival of corneal or other ocular tissue and are useful as surgical adjuncts in patients which are atopic or immune impaired.

The abstract of Barlett R. R. et al., entitled "Isoxazole-4-Carboxamides and Hydroxyalklidene-Cyanoacetamides, Drugs Containing These Compounds and Use of Such Drugs" PCT/EP90/01800, asserts:

Isoxazole-4-carboxamide derivatives and hydroxyalkylidene-cyanoacetamide derivatives are suitable for the treatment of cancer diseases. These compounds can be prepared by prior art methods. Some of them are new and are suitable, in addition, for the treatment of rheumatic diseases.

Bartlett et al., U.S. Pat. No. 5,268,382 (1993), mentions the use of leflunomide and N-(4-trifluoro-methylphenyl)-2-cyano-3-hydroxycrotonamide to combat chronic graft-versus-host diseases, and in particular systemic lupus erythematosus. Bartlett R. R. et al., *Agents and Actions* 32:10–21 (1991), indicates leflunomide was shown to be very effective in preventing and curing several autoimmune animal diseases.

Other publications concerning leflunomide include the following: Barlett et al., *Leflunomide: A novel immunomodulating drug in: Nonsteroidal Anti-Inflammatory Drugs* (2nd ed.) pp. 349–366, Eds. Lewis and Furst, Dekker, N.Y., N.Y.; *Pharmaprojects*, PJB Publications Lts, Richmond, Surrey, U.K.; *Hoechst Present Future Plans, in: R & D Focus Drug News*, Oct. 3, 1994; *Hoechst Licensing and R & D update, in: R & D Focus Drug News*, Feb. 10, 1992; *Leflunomide, in: R & D Focus Drug News*, May 23, 1994; Xiao et al., *Transplantation* 58:828–834, 1994; Xiao et al., *Transplantation* 26:1263–1265, 1994; McChesney et al., *Transplantation*, 57:1717–1722, 1994; Bartlett et al., *Springer Semin. Immunopathol.*, 14:381–394, 1993; Nichterlein et al., *Immunol. Infect. Dis.* 4:18–22, 1994; Williams et al., *Transplantation*, 57:1223–1231, 1994; Weithmann et al., entitled "Use of Leflunomide for the Inhibition of Interleukin 1.alpha.," EP 6077742 A2, 940727; Weithmann et al., entitled "Use of Leflunomide for the Inhibition of Interleukin 1.beta.," EP 607775 A2, 940727; Weithmann et al., entitled "Use of Leflunomide for the Inhibition of Tumor Necrosis Factor .alpha. (TNF-.alpha.)," EP 607776 A2, 940727; Weithmann et al., entitled "Use of Leflunomide for the Inhibition of Interleukin 8," EP 607777 A2, 940727; Ju et al., *Yaoxue Xuebao* 92:90–94, 1994; Weithmann et al., *Agents Actions*, 41:164–170, 1994; Ju et al., *Zhongguo Yaoli Xuebao*, 15:223–226, 1994; Chong et al., *Transplantation*, 55:1361–1366, 1993; Zielinski et al., *Agents Actions*, 38: (Special Conference Issue) C80–C82, 1993; Chong et al., *Transplant. Proc.*, 25:747–749, 1993; Williams et al., *Transplant. Proc.*, 25:745–746, 1993; Schorlemmer et al., *Transplant. Proc.*, 25:763–767, 1993; Glant et al., *Immunopharmacology*, 23:105–116, 1992; Ulrich et al., *Transplant. Proc.*, 24:718–719, 1992; Ogawa et al. *Clin. Immunol. Immunopathol.*, 61:103–118, 1991; Kuechle et al., *Transplant. Proc.*, 23:1083–1086, 1991; Ogawa et al, *Agents Actions*, 31:321–328, 1990; and Thoenes et al., *Int. J. Immunopharmacol.*, 11:921–929, 1989.

These references mentioned in the background section are each hereby incorporated by reference herein into the present application.

SUMMARY OF THE INVENTION

The present invention features compounds and methods for inhibiting hyper-proliferative cell growth. The compounds and methods are preferably used to treat patients having a hyper-proliferative cell disorder. The compounds are believed to act either directly on hyper-proliferating cells and/or on cells supporting hyper-proliferative cell growth. Hyper-proliferative cell growth of one cell can be supported by a different cell through different mechanisms, for example, vascularization of a tumor provides for nutrients to feed the tumor, and secretion of growth factors from one cell can stimulate the growth of another cell.

"Hyper-proliferative cell growth" refers to excess cell proliferation. The excess cell proliferation is relative to that occurring with the same type of cell in the general population and/or the same type of cell obtained from a patient at an earlier time. "Hyper-proliferative cell disorders" refer to disorders where an excess cell proliferation of one or more subsets of cells in a multicellular organism occurs resulting in harm (e.g., discomfort or decreased life expectancy) to the multicellular organism. The excess cell proliferation can be determined by reference to the general population and/or by reference to a particular patient (e.g., at an earlier point in the patient's life). Hyper-proliferative cell disorders can occur in different types of animals and in humans, and produce different physical manifestations depending upon the affected cells. Hyper-proliferative cell disorders include cancers, blood vessel proliferative disorders, fibrotic disorders, and autoimmune disorders.

Thus, a first aspect of the present invention features Structure I compounds able to inhibit hyper-proliferative cell growth having the chemical formula:

STRUCTURE I

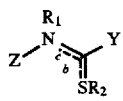

where $R_1$ is either hydrogen, alkyl, alkenyl, alkynyl, aryl, or is not present; preferably, $R_1$ is hydrogen;

$R_2$ is either aryl, alkyl, alkenyl, or alkynyl, or is not present; preferably $R_2$, is not present;

Y is selected from the group consisting of: aryl, alkyl, alkenyl, and alkynyl; preferably Y, is aryl or alkenyl;

Z is selected from the group consisting of: aryl, alkyl-aryl, alkenyl-aryl, and alkynyl-aryl; preferably, Z is aryl;

b is an optional additional bond; preferably, b is present as an additional bond; and c is an optional additional bond; preferably, c is not present;

provided that either b or c is present as an additional bond and if b is present as an additional bond $R_2$ is not present and c is not present, and if c is present as an additional bond $R_1$ is not present and b is not present; and pharmaceutically acceptable salts thereof.

The terms alkyl, alkenyl, alkynyl, aryl, alkyl-aryl, alkenyl-aryl, and alkynyl-aryl, including the preferred embodiments, are further described in Section I, infra.

A first preferred embodiment is described by Structure I.A compounds having the chemical formula:

STRUCTURE I.A

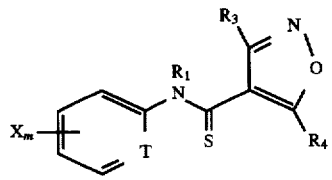

where T is carbon or nitrogen;

if T is carbon m is either 0, 1, 2, 3, 4 or 5; and if T is nitrogen m is either 0, 1, 2, 3, or 4;

each X is independently selected from the group consisting of: SH, OH, lower alkyl, lower alkenyl, lower alkoxy, haloalkoxy, halogen, haloalkyl, cyano, sulfonyl-aryl, amino, aminosulfonyl, and $NO_2$ $R_1$ is hydrogen or lower alkyl;

$R_3$ is selected from the group consisting of: hydrogen, carboxy, alkoxy, and carbalkoxy;

$R_4$ is selected from the group consisting of: alkyl, alkenyl, alkyl-aryl, alkenyl-aryl, and alkynyl-aryl; and pharmaceutically acceptable salts thereof.

The terms lower alkyl, lower alkenyl, alkoxy, carbalkoxy, haloalkoxy, and haloalkyl, including preferred embodiments, are further described in Section I, infra.

A second preferred embodiment is described by Structure I.B compounds having the chemical formula:

Structure I.B

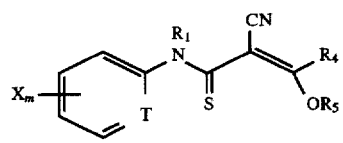

where $R_1$, $R_4$, T, each X, and m are as described for Structure I.A compounds; and $R_5$ is hydrogen or a group which is cleavable in vivo.

$OR_5$ can provide Structure I.B compounds with a prodrug structure. Structure I.B shows $OR_5$ as trans to CN, however, it should be understood that $OR_5$ may be cis to CN.

Examples of preferred Structure I compounds are AA10 (5-methyl-4-(4-trifluoromethylphenyl) aminothiocarbonylisoxazole), AA12 (1-cyano-2-hydroxy-1-(4-trifluoromethylphenylaminothiocarbonyl)propene), AA14 (1-cyano-2-hydroxy-1-(4-trifluoromethylphenylaminothiocarbonyl)propene sodium salt), Compound 6 (3-hydroxy-3-(propen-2-yl)-2-[(4-(trifluoro-methyl)-phenyl]aminothiocarbonyl]acrylonitrile), and Compound 3 (3-cyclopropyl-3-hydroxy-2-[(4-trifluoromethylphenyl)aminothiocarbonyl]acrylonitrile). AA14 which is a sodium salt of AA12, is an example of a Structure I compound formulated as a pharmaceutically acceptable salt.

"pharmaceutical acceptable salt" is a non-toxic salt of the compound which does not prevent the compound from exerting its effect on hyper-proliferative cell growth in a patient. Preferred pharmaceutical acceptable salts include sodium, potassium, ammonium, and aluminum salts, preferably the salt is a sodium salt.

Another aspect of the present invention features a Structure II compound which can inhibit hyper-proliferative cell growth having the chemical formula:

STRUCTURE II

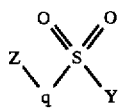

where Y and Z are as defined above for Structure I compounds;

q is either N-lower alkyl, NH, or a covalent bond; preferably, q is either NH or a covalent bond; and pharmaceutically acceptable salts thereof.

A first preferred embodiment is described by Structure II.A compounds having the chemical formula:

Structure II.A

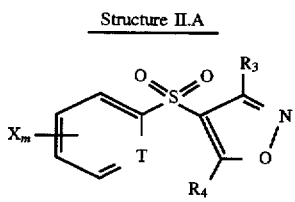

where each X, m, $R_3$, and $R_4$ is as described for Structure I.A compounds.

A second preferred embodiment is described by Structure II.B compounds having the chemical formula:

Structure II.B

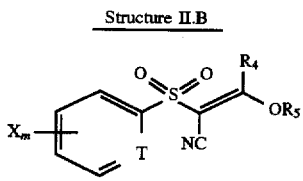

where T, m, $R_4$, $R_5$ and each X is as described for Structure I.B compounds.

A third preferred embodiment is described by Structure II.C compounds having the chemical formula:

Structure II.C

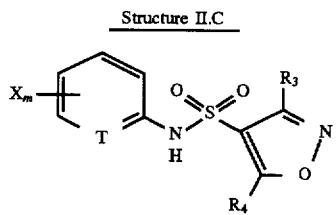

where T, m, $R_3$, $R_4$ and each X is as described f or Structure I.A compounds.

A fourth preferred embodiment is described by Structure II.D compounds having the chemical formula:

Structure II.D

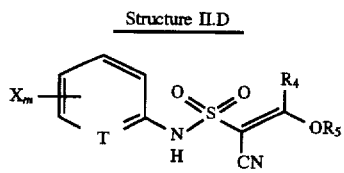

where T, m, $R_4$, $R_5$ and each X is as described for Structure I.B compounds.

Examples of preferred Structure I and II compounds include AA11 (4-(4-chlorophenylsulfonyl)-5-methylisoxazole), AA13 (1-(4-chlorophenylsulfonyl)-1-cyano-2-hydroxypropene), AA15 (1-(4-chlorophenylsulfonyl)-1-cyano-2-hydroxypropene sodium), AA16 (4-(4-trifluoromethylphenylaminosulfonyl)-5-methylisoxazole), AA17 (1-cyano-2-hydroxy-1-(4-trifluoromethylphenylaminosulfonyl)propene) and AA18(1-cyano-2-hydroxy-1-(4-trifluoromethylphenylaminosulfonyl)propene sodium salt). AA15 which is a sodium salt of AA13, is an example of a Structure II compound formulated as a pharmaceu- tically acceptable salt.

Another aspect of the present invention features a pharmaceutical composition comprising a pharmaceutically acceptable carrier and a Structure I or II compound described herein. The pharmaceutical composition contains the Structure I or II compound in a form suitable for administration into a patient. Preferably, the pharmaceutical composition contains an amount of a Structure I or Structure II compound in a proper pharmaceutical dosage form sufficient to exert a therapeutic effect on a patient. However, multiple doses of pharmaceutical compositions may be used to treat a patient.

Considerations and factors concerning dosage forms suitable for administration are known in the art and include potential toxic effects, solubility, route of administration, and maintaining activity. For example. pharmaceutical compositions injected into the bloodstream should be soluble.

Other aspects of the present invention feature methods of inhibiting hyper-proliferative cell growth using a Structure I or a Structure II compound, and methods of treating a patient having a hyper-proliferative cell disorder by administering to the patient a therapeutically effective amount of a Structure I or II compound.

Hyper-proliferative cell growth can be inhibited using a growth inhibiting amount of a Structure I or II compound (i.e., an amount sufficient to inhibit the growth of a cell exhibiting hyper-proliferative cell growth). The methods can be used to treat a patient using in vivo or ex vivo procedures. In vivo procedures involve directly administering the compound to a patient, generally as part of a pharmaceutical composition. In ex vivo procedures, cells are removed from a patient, exposed to a sufficient amount of compound to inhibit cell growth, and then reintroduced into a patient.

Preferably, the compounds are used to treat a human patient suffering from a hyper-proliferative cell disorder by administering a therapeutically effective amount of the compound to the patient.

A "therapeutically effective amount," in reference to the treatment of a cancer refers to an amount sufficient to bring about one or more of the following results: reduce the size of the cancer; inhibit the metastasis of the cancer; inhibit the growth of the cancer, preferably stop cancer growth; relieve discomfort due to the cancer; and prolong the life of a patient inflicted with the cancer.

A "therapeutically effective amount," in reference to the treatment of a hyper-proliferative cell disorder other than a cancer refers to an amount sufficient to bring about one or more of the following results: inhibit the growth of cells causing the disorder, preferably stopping the cell growth; relieve discomfort due to the disorder; and prolong the life of a patient suffering from the disorder.

Structure I and II compounds can be used alone or with other agents which inhibit hyper-proliferative cell growth. For example, the compounds can be used to treat a cancer in conjunction with standard anti-cancer agents.

Thus, the present invention features two different groups of compounds (Structure I and Structure II) able to inhibit hyper-proliferative cell growth. Examples of specific compounds falling within these groups are provided along with guidelines to obtain related compounds able to inhibit hyper-proliferative cell growth. For example, Structure I and Structure II compounds can be synthesized using standard synthesis techniques and the guidelines provided herein, and the ability of such compounds to inhibit a particular hyper-proliferative cell disorder then can be determined using standard techniques to obtain therapeutically effective Structure I and Structure II compounds.

Other features and advantages of the invention will be apparent from the following figures, detailed description of the invention, examples, and the claims.

DETAILED DESCRIPTION OF THE INVENTION

Figure 1:
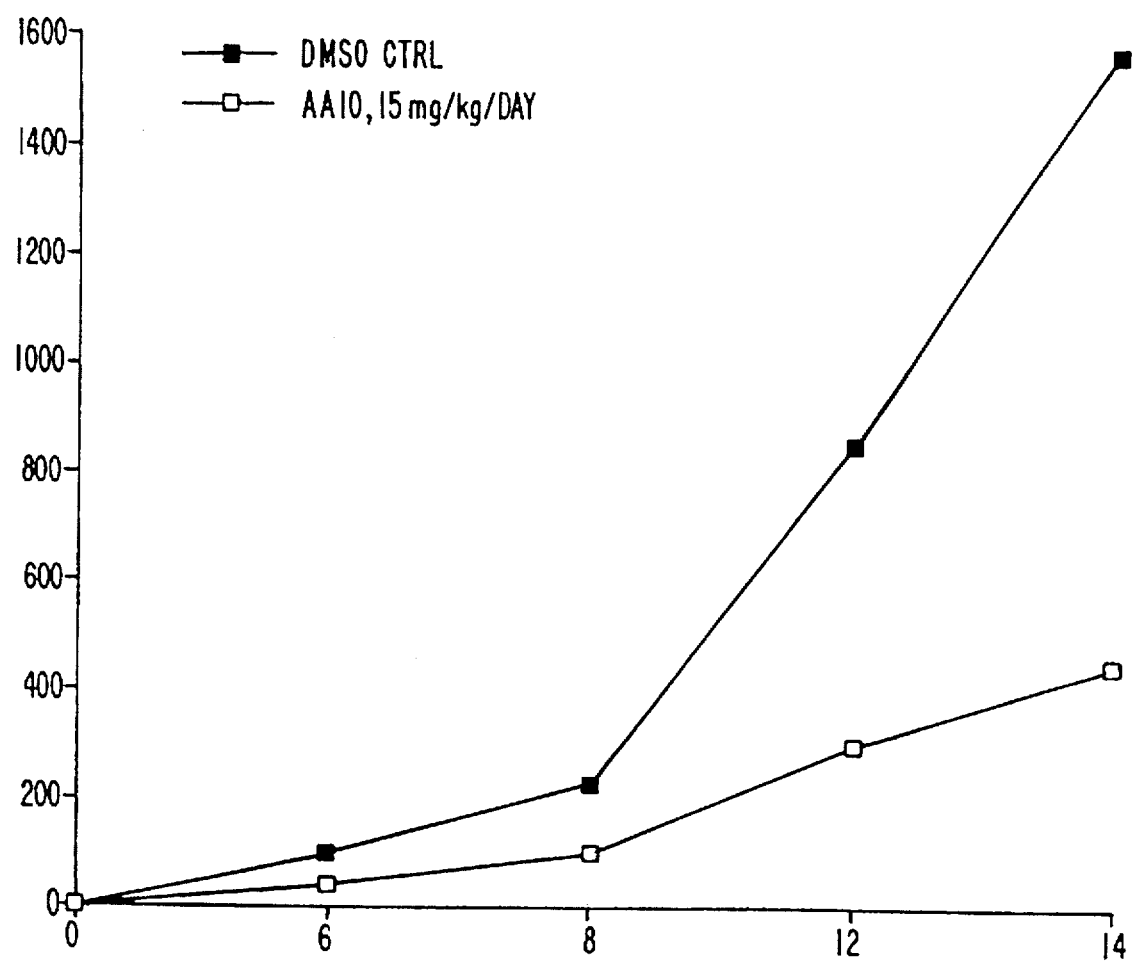
FIG. 1 illustrates the ability of AA10 to inhibit glioma cells in a Xenograft model.

The present invention features arylaminothiocarbonyl derivative compounds and arylsulfonyl derivative compounds. The compounds can be used to treat various hyper-proliferative cell disorders such as those described herein (including the Background of the Invention supra), those described by Hirth et al., entitled "Treatment of Platelet Derived Growth Factor Related Disorders Such as Cancers" U.S. Ser. No. 08/370,574 (SUGEN Inc., the assignee of the present invention is a joint assignee of U.S. Ser. No. 08/370, 574 which is hereby incorporated by reference into the present application), and those described by Hirth et al., entitled "Treatment of Platelet Derived Growth Factor Related Disorders Such as Cancers," incorporated by reference herein into the present application PCT/US/00363, International Publication WO 95/19169.

Without being bound to any particularly theory, or mode of action of the compounds described herein, the compounds may be active at the platelet derived growth factor receptor (PDGF-R) and related receptor kinases such as Flt and KDR as described by U.S. Ser. No. 08/370,574. PDGF-R, Flt and KDR are discussed in more detail by Heldin, C-H, *EMBO Journal* 11:4251–4259, 1992; Plate et al., *Laboratory Investigation* 4:529–534, 1992; Plate et al., *Nature* 359:845–848, 1992; Shweiki et al., *Nature* 359:843–845, 1992; Millauer et al., *cell* 72:835–846, 1993; Plate et al., *Cancer Res.*, 53:5822–5827, 1993; and Waltenberger et al., *Journal of Biological Chemistry* 43:26988–26995, 1994 (each of these references are hereby incorporated by reference herein).

While the compounds described herein are believed to act at PDGF-R and related receptor kinases such as Flt and KDR, unless otherwise explicitly stated in the claims that a compound exerts an effect by acting at a receptor, there is no intention to limit the claimed methods to those requiring inhibition of receptor kinase activity. Rather, the present application demonstrates that compounds able to effect PDGF-R and related receptor kinases such as Flt and KDR, whose ability to inhibit receptor activity can be measured in vivo or in vitro, exert significant physiological effects.

Preferably, the compound has an $IC_{50}$ (amount of agent needed to achieve a 50% inhibition of cell growth) of 10 µM or less as determined by the growth assay described in the examples below.

Thus, the present application demonstrates the ability of different compounds able to inhibit PDGF-R and related receptor kinases activity to inhibit hyper-proliferative cell growth such as tumor growth. Compounds used for cancer treatment preferably achieve at least a 50 inhibition in tumor growth after a twelve day treatment using the animal models described in the examples below.

I. Chemical Definitions

The following is a list of definitions for some of the chemical groups described in the present disclosure.

An "amino" refers to —$NH_2$.

A "substituted amino" refers to $R_1$—NH—$R_2$ where $R_1$ and $R_2$ are groups which may be the same or different.

An "alkyl" refers to a saturated aliphatic hydrocarbon, including straight-chain, branched-chain, and cyclic alkyl groups. Preferably, the alkyl group has 1 to 12 carbons, more preferably, 1 to 7 carbons, even more preferably, 1 to 4 carbons. The alkyl may be unsubstituted or may contain one or more substitutions. Multiple substitutions can be made having the same or different substituents. Preferred substitution substituents are hydroxyl, cyano, lower-alkoxy, =O, =S, $NO_2$, $N(CH_3)_2$, amino, and SH. Preferably, the alkyl has no more than three substitution substituents. More preferably, the alkyl is a lower alkyl, which is an unsubstituted branched-, straight-chain, or cyclic alkyl, 1 to 7 carbons in length, preferably 1 to 4 carbons in length.

An "alkenyl" refers to an unsaturated hydrocarbon group containing at least one carbon-carbon double bond, including straight-chain, branched-chain, and non-aromatic cyclic groups.

Preferably, the alkenyl group has 2 to 12 carbons, more preferably, 2 to 7 carbons, more preferably, 2 to 4 carbons. The alkenyl may be unsubstituted or may contain one or more substitutions. Multiple substitutions can be made having the same or different substituents. Preferred substitution substituents are hydroxyl, cyano, lower-alkoxy, =O, =S, $NO_2$, $N(CH_3)_2$, amino, and SH. Preferably, the alkenyl has no more than three substitution substituents. More preferably, the alkenyl is a lower alkenyl, which is an unsubstituted branched-, straight-chain, or cyclic alkenyl 2 to 7 carbons in length, preferably 2 to 4 carbons in length.

An "alkynyl" refers to an unsaturated hydrocarbon group containing at least one carbon-carbon triple bond, including straight-chain, branched-chain, and non-aromatic cyclic groups. Preferably, the alkynyl group has 2 to 12 carbons, more preferably, 2 to 7 carbons, even more preferably 2 to 4 carbons. The alkynyl may be unsubstituted or may contain one or more substitutions. Multiple substitutions can be made having the same or different substituents. Preferred substitution substituents are hydroxyl, cyano, lower-alkoxy, =O, =S, $NO_2$, $N(CH_3)_2$, amino, and SH. Preferably, the alkynyl has no more than three substitution substituents. More preferably, the alkynyl is a lower alkynyl, which is an unsubstituted branched-, straight-chain, or cyclic alkynyl 2 to 7 carbons in length, preferably 2 to 4 carbons.

An "alkoxy" refers to O-alkyl, where alkyl is defined as described above. A lower alkoxy refers to O-lower alkyl.

An "aryl" refers to an aromatic group which has at least one ring having a conjugated pi electron system and includes carbocyclic aryl, heterocyclic aryl and biaryl groups, containing up to two conjugated or fused ring systems, all of which may be optionally substituted. Preferred aryl substitution substituents are each independently selected from the group consisting of: alkoxy, haloalkoxy, haloalkyl, sulfonylaryl, aminosulfonyl, halogen, trihalomethyl, hydroxyl, SH, OH, $NO_2$, amine, cyano, lower-alkoxy, lower-alkyl, lower-alkenyl, lower-alkynyl, amino, carboxy, and carbalkoxy. Preferably, the aryl contains no more than five substitution substituents, more preferably the aryl has one to four substitution substituents, more preferably the aryl has one to three substitution substituents.

A "carbocyclic aryl" refers to an aryl where the ring atoms on the aromatic ring are all carbon atoms. The carbon atoms are optionally substituted as described above for an aryl.

A "heterocyclic aryl" is an aryl having from 1 to 3 heteroatoms as ring atoms in the aromatic ring and the remainder of the ring atoms are carbon atoms. Suitable heteroatoms include oxygen, sulfur, and nitrogen. Examples of heterocyclic aryls include furanyl, thienyl, pyridyl, pyrrolyl, N-lower alkyl pyrrolo, pyrimidyl, pyrazinyl, imidazolyl, isoxazole, which may be substituted as described above for an aryl.

A "carbalkoxy" group refers to a COOX group, where "X" is a lower alkyl.

"Haloalkyl" refers to substituted alkyl, having no more than 4 carbons, where the substituents are halogens and at least one halogen is present. Preferably, the haloalkyl is 1 to 3 carbons in length and the halogens are each independently either Cl or F, more preferably, the alkyl has 2 carbons, more preferably the haloalkyl is a lower haloalkyl which has 1 carbon.

"Haloalkoxy" refers to oxygen joined to a "haloalkyl." Preferably, the haloalkoxy is a "lower-haloalkoxy," which is an oxygen joined to a lower-haloalkyl.

II. Structure I Compounds

Structure I compounds are arylaminothiocarbonyl derivatives having the chemical formula:

STRUCTURE I

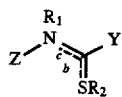

where $R_1$ is either hydrogen, alkyl, alkenyl, alkynyl, aryl, or is not present; preferably, $R_1$ is hydrogen;

$R_2$ is either hydrogen, aryl, alkyl, alkenyl, or alkynyl, or is not present; preferably $R_2$ is either hydrogen a lower alkyl, or is not present; more preferably, $R_2$ is not present;

Y is selected from the group consisting of: aryl, alkyl, alkenyl, and alkynyl; preferably Y, is aryl or alkenyl;

Z is selected from the group consisting of: aryl, alkyl-aryl, alkenyl-aryl, and alkynyl-aryl; preferably, Z is aryl;

b is an optional additional bond; preferably, b is present as an additional bond; and c is an optional additional bond; preferably, c is not present;

provided that either b or c is present as an additional bond and if b is present as an additional bond $R_2$ is not present and c is not present, and if c is present as an additional bond $R_1$ is not present and b is not present; and pharmaceutically acceptable salts thereof.

A. Structure I.A Compounds

A first preferred group of arylaminothiocarbonyl derivatives is described by Structure I.A compounds having the chemical formula:

STRUCTURE I.A

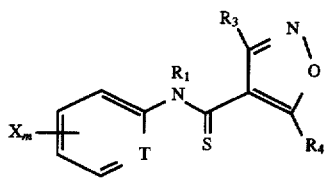

where T is either carbon or nitrogen; preferably, T is carbon;

$R_1$ is either hydrogen or lower alkyl; preferably, $R_1$ is hydrogen;

$R_3$ is selected from the group consisting of: hydrogen, carboxy, alkoxy, and carbalkoxy; preferably, $R_3$ is either hydrogen, carboxy, lower alkoxy, or carbalkoxy; more preferably, $R_3$ is hydrogen;

$R_4$ is selected from the group consisting of: alkyl, alkenyl, alkyl-aryl, alkenyl-aryl, and alkynyl-aryl; preferably, $R_4$ is either lower alkyl or lower alkenyl; more preferably $R_4$ is either $CH_3$, cyclopropyl, allyl, isopropyl, or 2-propenyl;

if T is carbon m is 0, 1, 2, 3, 4 or 5; and if T is nitrogen, m is 0, 1, 2, 3, or 4; preferably, m is either 1, 2, 3, or 4; more preferably, m is 1, 2, or 3; more preferably, m is 1 or 2; and even more preferably, m is 1;

each X is independently selected from the group consisting of: SH, OH, lower alkyl, lower alkenyl, lower alkoxy, haloalkoxy, halogen, haloalkyl, cyano, sulfonyl-aryl, amino, aminosulfonyl, and $NO_2$; preferably, each X is independently selected from the group consisting of: SH, OH, lower alkyl, lower alkenyl, lower alkoxy, haloalkoxy, halogen, haloalkyl, cyano, piperidine-1-sulfonyl, amino, aminosulfonyl, and $NO_2$; more preferably, each X is independently selected from the group consisting of: halogen, lower haloalkyl, lower haloalkoxy, piperidine-1-sulfonyl, aminosulfonyl, and cyano; more preferably, each X is independently selected from the group consisting of: $CF_3$, $OCF_3$, Fl, Cl, Br, piperidine-1-sulfonyl, aminosulfonyl, and cyano; preferably, an X substituent is in the para position;

and pharmaceutically acceptable salts thereof.

B. Structure I.B Compounds

A second preferred group of arylaminothiocarbonyl derivatives is described by Structure I.B compounds having the chemical formula:

Structure I.B

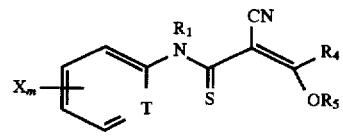

where $R_1$, $R_4$, T, each X, and m are as described for Structure I.A compounds, including preferred embodiments;

$R_5$ is hydrogen or a group which is cleavable in vivo; preferably, $R_5$ is selected from the group consisting of: alkyl, C(=O)-aryl, C(=O)-alkyl, C(=O)-alkenyl, C(=O)-alkynyl, hydrogen,

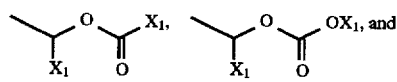

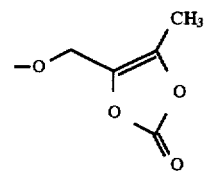

where each $X_1$ is independently alkyl or hydrogen; more preferably $R_5$ is selected from the group consisting of: lower alkyl, C(=O)-lower alkyl, C(=O)-lower alkenyl, hydrogen,

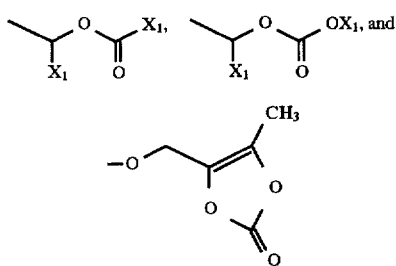

where each $X_1$ is independently lower alkyl or hydrogen; even more preferably, each $X_1$ is lower alkyl; and pharmaceutically acceptable salts thereof.

Structure I.A compounds appear to be produced in vivo from the corresponding Structure I.B compounds. For example, it is believed that AA12 is produced in vivo from AA10 by the opening of the heterocyclic ring, by the same mechanism in which N-(4-trifluoromethylphenyl)-2-cyano-3-hydroxycrotonamide is produced from leflunomide.

Additionally, the Structure I.B $R_5$ cleavable group is believed to allow the compound to act as a prodrug in vivo. For example, Patterson et al., *J. Med. Chem.* 35:507–510 (1992) (hereby incorporated by reference herein), describe a carboxy derivative of leflunomide which, like leflunomide, can act as a prodrug for N-(4-trifluoromethylphenyl)-2-cyano-3-hydroxycrotonamide.

The solubility of compounds AA10, AA12 and AA14 are illustrated in Table I.

TABLE I

| Compound | Solubility |
| --- | --- |
| AA10 | ≧1,000 mg/ml in DMSO |
| AA12 | 40 mg/ml in DMSO |
| AA14 | 275 mg/ml in PBS |

PBS refers to phosphate buffered saline at pH 7.4

Compound AA14 is soluble in PBS in contrast to the anti-hyper-proliferative compounds leflunomide and N-(4-trifluoromethylphenyl)-2-cyano-3-hydroxycrotonamide. The increased solubility of AA14 offers several advantages, for example, a larger amount of AA14 can be added at one time to achieve a longer effect thereby decreasing the need for continuous dosing, a larger amount of drug may be needed to achieve a particular therapeutic effect, and the increase in solubility reduces the need for formulations which can have adverse side effects.

Compound AA10 in addition to differing structurally from leflunomide is also more soluble in ethanol and appears to be more stable than leflunomide. The increase in stability offer advantages, for example, a larger amount of AA10 can be added at one time to achieve a longer effect thereby decreasing the need for continuous dosing.

Also as described in the examples below, both AA10 and AA12 were able to inhibit hyper-proliferative cell growth. It could be that both AA10 and AA12 are active in inhibiting hyper-proliferative cell growth. Alternatively, the observed growth inhibition may be due primarily to AA12, and AA10 may act primarily as a prodrug.

Representative examples of Structure I.B. compounds are shown in Table II.

TABLE II

| Compound # | X substituents | $R_4$ | $R_5$ | T |
| --- | --- | --- | --- | --- |
| AA12 | 4-trifluoromethyl | methyl | H | C |
| AA14 | 4-trifluoromethyl | methyl | Na | C |
| 3 | 4-trifluoromethyl | cyclopropyl | H | C |
| 4 | 4-trifluoromethyl | allyl | H | C |
| 5 | 4-trifluoromethyl | isopropyl | H | C |
| 6 | 4-trifluoromethyl | 2-propenyl | H | C |
| 7 | 2-bromo-4-fluoro | methyl | H | C |
| 8 | 2-bromo-4-fluoro | cyclopropyl | H | C |
| 9 | 2-bromo-4-fluoro | allyl | H | C |
| 10 | 2-bromo-4-fluoro | isopropyl | H | C |
| 11 | 2-bromo-4-fluoro | 2-propenyl | H | C |
| 12 | 2-trifluoromethyl | methyl | H | C |
| 13 | 2-trifluoromethyl | cyclopropyl | H | C |
| 14 | 2-trifluoromethyl | allyl | H | C |
| 15 | 2-trifluoromethyl | isopropyl | H | C |
| 16 | 2-trifluoromethyl | 2-propenyl | H | C |
| 17 | 3-trifluoromethyl | methyl | H | C |
| 18 | 3-trifluoromethyl | cyclopropyl | H | C |
| 19 | 3-trifluoromethyl | allyl | H | C |
| 20 | 3-trifluoromethyl | isopropyl | H | C |
| 21 | 3-trifluoromethyl | 2-propenyl | H | C |
| 22 | 4-(piperidine-1-sulfonyl) | methyl | H | C |
| 23 | 4-(piperidine-1-sulfonyl) | cyclopropyl | H | C |
| 24 | 4-(piperidine-1-sulfonyl) | allyl | H | C |
| 25 | 4-(piperidine-1-sulfonyl) | isopropyl | H | C |
| 26 | 4-(piperidine-1-sulfonyl) | 2-propenyl | H | C |
| 27 | 4-aminosulfonyl | methyl | H | C |
| 28 | 4-aminosulfonyl | cyclopropyl | H | C |
| 29 | 4-aminosulfonyl | allyl | H | C |
| 30 | 4-aminosulfonyl | isopropyl | H | C |
| 31 | 4-aminosulfonyl | 2-propenyl | H | C |
| 32 | 2,3-dichloro | methyl | H | C |
| 33 | 2,3-dichloro | cyclopropyl | H | C |
| 34 | 2,3-dichloro | allyl | H | C |
| 35 | 2,3-dichloro | isopropyl | H | C |
| 36 | 2,3-dichloro | 2-propenyl | H | C |
| 37 | 3,4-dichloro | methyl | H | C |
| 38 | 3,4-dichloro | cyclopropyl | H | C |
| 39 | 3,4-dichloro | allyl | H | C |
| 40 | 3,4-dichloro | isopropyl | H | C |
| 41 | 3,4-dichloro | 2-propenyl | H | C |
| 42 | 2,4-dichloro | methyl | H | C |
| 43 | 2,4-dichloro | cyclopropyl | H | C |
| 44 | 2,4-dichloro | allyl | H | C |
| 45 | 2,4-dichloro | isopropyl | H | C |
| 46 | 2,4-dichloro | 2-propenyl | H | C |
| 47 | 4-trifluoromethoxy | methyl | H | C |
| 48 | 4-trifluoromethoxy | cyclopropyl | H | C |
| 49 | 4-trifluoromethoxy | allyl | H | C |
| 50 | 4-trifluoromethoxy | isopropyl | H | C |
| 51 | 4-trifluoromethoxy | 2-propenyl | H | C |
| 52 | 3,5-di-trifluoromethyl | methyl | H | C |
| 53 | 3,5-di-trifluoromethyl | cyclopropyl | H | C |
| 54 | 3,5-di-trifluoromethyl | allyl | H | C |
| 55 | 3,5-di-trifluoromethyl | isopropyl | H | C |
| 56 | 3,5-di-trifluoromethyl | 2-propenyl | H | C |
| 57 | 2-fluoro | methyl | H | C |
| 58 | 2-fluoro | cyclopropyl | H | C |
| 59 | 2-fluoro | allyl | H | C |
| 60 | 2-fluoro | isopropyl | H | C |
| 61 | 2-fluoro | 2-propenyl | H | C |
| 62 | 2,4-difluoro | methyl | H | C |
| 63 | 2,4-difluoro | cyclopropyl | H | C |
| 64 | 2,4-difluoro | allyl | H | C |
| 65 | 2,4-difluoro | isopropyl | H | C |
| 66 | 2,4-difluoro | 2-propenyl | H | C |
| 67 | 2,6-difluoro | methyl | H | C |
| 68 | 2,6-difluoro | cyclopropyl | H | C |
| 69 | 2,6-difluoro | allyl | H | C |
| 70 | 2,6-difluoro | isopropyl | H | C |
| 71 | 2,6-difluoro | 2-propenyl | H | C |
| 72 | 2,4,6-trifluoro | methyl | H | C |
| 73 | 2,4,6-trifluoro | cyclopropyl | H | C |
| 74 | 2,4,6-trifluoro | allyl | H | C |
| 75 | 2,4,6-trifluoro | isopropyl | H | C |
| 76 | 2,4,6-trifluoro | 2-propenyl | H | C |
| 77 | 2-chloro-3-trifluoromethyl | methyl | H | C |

TABLE II-continued

| Compound # | X substituents | R₄ | R₅ | T |
|---|---|---|---|---|
| 78 | 2-chloro-3-trifluoromethyl | cyclopropyl | H | C |
| 79 | 2-chloro-3-trifluoromethyl | allyl | H | C |
| 80 | 2-chloro-3-trifluoromethyl | isopropyl | H | C |
| 81 | 2-chloro-3-trifluoromethyl | 2-propenyl | H | C |
| 82 | 4-bromo-2-trifluoromethyl | methyl | H | C |
| 83 | 4-bromo-2-trifluoromethyl | cyclopropyl | H | C |
| 84 | 4-bromo-2-trifluoromethyl | allyl | H | C |
| 85 | 4-bromo-2-trifluoromethyl | isopropyl | H | C |
| 86 | 4-bromo-2-trifluoromethyl | 2-propenyl | H | C |
| 87 | 4-chloro-3-trifluoromethyl | methyl | H | C |
| 88 | 4-chloro-3-trifluoromethyl | cyclopropyl | H | C |
| 89 | 4-chloro-3-trifluoromethyl | allyl | H | C |
| 90 | 4-chloro-3-trifluoromethyl | isopropyl | H | C |
| 91 | 4-chloro-3-trifluoromethyl | 2-propenyl | H | C |
| 92 | 2-cyano-3-fluoro | methyl | H | C |
| 93 | 2-cyano-3-fluoro | cyclopropyl | H | C |
| 94 | 2-cyano-3-fluoro | allyl | H | C |
| 95 | 2-cyano-3-fluoro | isopropyl | H | C |
| 96 | 2-cyano-3-fluoro | 2-propenyl | H | C |
| 97 | 3,4-difluoro | methyl | H | C |
| 98 | 3,4-difluoro | cyclopropyl | H | C |
| 99 | 3,4-difluoro | allyl | H | C |
| 100 | 3,4-difluoro | isopropyl | H | C |
| 101 | 3,4-difluoro | 2-propenyl | H | C |
| 102 | 5-trifluoromethyl | methyl | H | N |
| 103 | 5-trifluoromethyl | cyclopropyl | H | N |
| 104 | 5-trifluoromethyl | allyl | H | N |
| 105 | 5-trifluoromethyl | isopropyl | H | N |
| 106 | 5-trifluoromethyl | 2-propenyl | H | N |
| 107 | 5-cyano | methyl | H | N |
| 108 | 5-cyano | cyclopropyl | H | N |
| 109 | 5-cyano | allyl | H | N |
| 110 | 5-cyano | isopropyl | H | N |
| 111 | 5-cyano | 2-propenyl | H | N |

III. Structure II Compounds

Structure II compounds are arylsulfonyl derivatives having the following Structure.

STRUCTURE II

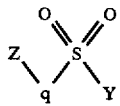

where Y and Z are as defined above for Structure I compounds, including preferred embodiments;

q is N-lower alkyl, NH, or a covalent bond; preferably, q is either NH or a covalent bond; and pharmaceutically acceptable salts thereof.

A. Structure II.A Compounds

A first preferred group of arylsulfonyl derivatives are Structure II.A compounds having the chemical formula:

Structure II.A

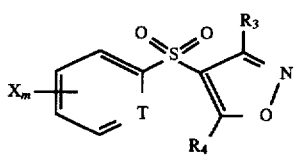

where each X, m, T, R₃, and R₄ is as described for Structure I.A compounds, including preferred embodiments; and pharmaceutically acceptable salts thereof.

B. Structure II.B Compounds

A second preferred group of arylsulfonyl derivatives are Structure II.B compounds having the chemical formula:

Structure II.B

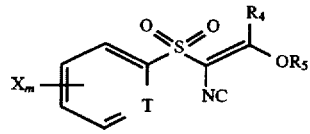

where T, m, R₄, R₅ and each X, is as described for Structure I.B compounds, including preferred embodiments; and pharmaceutically acceptable salts thereof.

It appears that Structure II.B compounds can be formed in vivo from the Structure II.A compounds by opening of the Structure II.B heterocyclic ring.

C. Structure II.C Compounds

A third preferred group of arylsulfonyl derivatives are Structure II.C compounds having the chemical formula:

Structure II.C

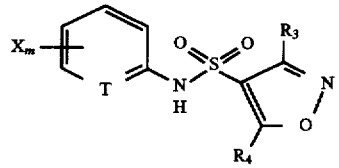

where T, m, R₃, R₄, and each X, is as described for Structure I.A compounds, including preferred embodiments; and pharmaceutically acceptable salts thereof.

D. Structure II.D Compounds

A fourth preferred group of arylsulfonyl derivatives are Structure II.D compounds having the chemical formula:

Structure II.D

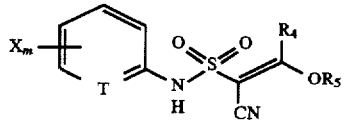

where T, m, R₄, R₅ and each X is as described for Structure I.B compounds, including preferred embodiments; and pharmaceutically acceptable salts thereof.

It appears that Structure II.C compounds can be formed in vivo from the Structure II.D compounds by opening of the Structure II.C heterocyclic ring.

IV. Hyper-Proliferative Cell Disorders

Hyper-proliferative cell disorders include cancers, blood vessel proliferation disorders, fibrotic disorders, autoimmune disorders, and graft-versus-host rejection. The Background of the Invention provides examples of different types of diseases or disorders which can be treated by the present invention. The different diseases or disorders described herein are not necessarily independent. For example, fibrotic disorders may be related to, or overlap with, blood vessel disorders. For example, atherosclerosis (which is characterized herein as a blood vessel disorder) results in the abnormal formation of fibrous tissue.

Blood vessel proliferation disorders refer to angiogenic and vasculogenic disorders generally resulting in abnormal proliferation of blood vessels. Examples of such disorders include restenosis, retinopathies, and atherosclerosis. The advanced lesions of atherosclerosis result from an excessive inflammatory-proliferative response to an insult to the endothelium and smooth muscle of the artery wall. (Ross R., *Nature* 362:801–809 (1993).) Part of the response appears to be mediated by PDGF-BB secretion, and activation of PDGF-R in endothelial and smooth muscle cells. Both cell migration and cell proliferation play a role in the formation of atherosclerotic lesions.

Fibrotic disorders are due to the abnormal formation of an extracellular matrix. Examples of fibrotic disorders include hepatic cirrhosis and mesangial proliferative cell disorders. Hepatic cirrhosis is characterized by the increase in extracellular matrix constituents resulting in the formation of a hepatic scar. Hepatic cirrhosis can cause diseases such as cirrhosis of the liver. An increased extracellular matrix resulting in a hepatic scar can also be caused by viral infection such as hepatitis. Lipocytes appear to play a major role in hepatic cirrhosis. Inappropriate PDGF-R activity can stimulate lipocyte proliferation.

Mesangial disorders are brought about by abnormal proliferation of mesangial cells. Mesangial hyper-proliferative cell disorders include various human renal diseases, such as glomerulonephritis, diabetic nephropathy, malignant nephrosclerosis, thrombotic microangiopathy syndromes, transplant rejection, and glomerulopathies.

Cancers can be caused by abnormal growth of different types of cells. A "cancer cell" refers to various types of malignant neoplasms, most of which can invade surrounding tissues and may metastasize to different sites, as defined by Stedman's Medical Dictionary 25th edition (Hensyl ed. 1990). Examples of cancers which may be treated by the present invention include solid tumors such as intra-axial brain cancers, ovarian cancers, colon cancers, prostate cancers, lung cancers, Kaposi's sarcoma and skin cancers; and leukemia. Preferably, the compounds described herein are used to treat solid tumors.

These different types of cancers can be further characterized. For example, intra-axial brain cancers include glioblastoma multiforme, anaplastic astrocytoma, astrocytoma, ependymoma, oligodendroglioma, medulloblastoma, meningioma, sarcoma, hemangioblastoma, and pineal parenchymal.

The formation and spreading of blood vessels, or vasculogenesis and angiogenesis respectively, play important roles in a variety of physiological processes such as embryonic development, wound healing and organ regeneration. They also play a role in cancer development by facilitating vascularization of solid tumors. Thus, solid tumor growth can be inhibited through different mechanisms such as directly inhibiting the growth of tumor cells and/or inhibiting the growth of cells supporting tumor growth.

a. Ovarian cancer

Epithelial ovarian cancer accounts for nearly 90% of all ovarian tumors and continues to be a highly lethal malignancy. Treatment for advanced ovarian cancer generally includes cytoreductive surgery followed by combination chemotherapy with alkylating agents such as cisplatin and cyclophosphamide. However, long term survival of advanced ovarian cancer patients is extremely poor, in the range of 10%–20%, principally because of the high incidence of metastatic tumors throughout the peritoneal cavity, and, in some cases, the lymph-nodes. Moreover, chemotherapy with cisplatin carries a potential for renal toxicity and progressive neuropathy.

Treatment of ovarian cancers can be carried out by administering a Structure I or II compound to supporting stromal cells (i.e., the framework upon which a tumor or metastatic lesion grows, including but not limited to connective tissue and vascular endothelial cells), and/or in associated vascular endothelial cells. In view of the localized spread of ovarian cancer throughout the peritoneal cavity, a preferred method of administration, particularly in advanced cases, is by intravenous or intraperitoneal injection.

B. Glioma

The compounds described herein can also be used in the treatment of primary intra-axial brain tumors of the glioma family, such as astrocytomas and glioblastomas. Glioblastoma multiforme is the most common and most malignant tumor of astrocytic origin in human adults and accounts for more than half of all primary brain tumors (see, for example, *Cecil Textbook of Medicine*, Wyngaarden, Smith, Bennett (eds) WB Saunders, 1992, p. 2220).

Gliomas have the common property of direct invasive involvement of brain tissue, are fundamentally malignant, and are inevitably fatal. Glioblastoma patients have a median survival time of less than one year even when treated aggressively with a combination of surgery, chemotherapy, and radiotherapy. Unfortunately, successful surgical intervention is extremely rare in view of the difficulty or impossibility of defining the microscopic borders of a glioma within normal brain tissue. Similarly, chemotherapy with alkylating agents has met with very little success, and no more than 10% of glioma patients respond significantly. Radiation therapy has demonstrated some value in controlling the growth of gliomas, but often results in substantial neurologic impairment. Therapy with interferon-β, in combination with radiotherapy and chemotherapy, has met with some success (DeVita, Hellman, Rosenberg (eds) *Biologic Therapy of Cancer*, J. B. Lippincott, 1991).

Intravenous and intra-arterial routes are considered to be preferred routes of administration. In addition, microcatheter technology may be particularly effective at delivering the compositions of the invention directly to the site of the glioma, thereby achieving immediate localized contact with the cancer and proximate endothelial cells and possibly minimizing potential toxicity associated with more distal intra-arterial delivery.

V. Compound Administration a. Formulations

The compounds of the present invention can be administered to a patient alone, or in a pharmaceutical composition comprising the active compound and a carrier or excipient. The compounds also can be prepared as pharmaceutically acceptable salts. Examples of pharmaceutically acceptable salts include acid addition salts such as those containing hydrochloride, sulfate, phosphate, sulfamate, acetate, citrate, lactate, tartrate, methanesulfonate, ethanesulfonate, benzenesulfonate, p-toluenesulfonate, cyclohexylsulfamate and quinate. (See e.g., supra, PCT/US92/03736). Such salts can be derived using acids such as hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid.

Pharmaceutically acceptable salts can be prepared by standard techniques. For example, the free base form of the compound is first dissolved in a suitable solvent such as an aqueous or aqueous-alcohol solution, containing the appropriate acid. The salt is then isolated by evaporating the solution. In another example, the salt is prepared by reacting the free base and acid in an organic solvent.

Pharmaceutically acceptable salts also include basic addition salts such as those containing benzathine, chloroprocaine, choline, diethanolamine, ethylenediamine, meglumine, procaine, aluminum, calcium, lithium, magnesium, potassium, sodium, ammonium, alkylamine, and zinc. For example, see *Remington's Pharmaceutical Sciences*, 18th ed., Mack Publishing Co., Easton, Pa., p. 1445, 1990. Such salts can be prepared using the appropriate corresponding bases.

Carriers or excipients can be used to facilitate administration of the compound, for example, to increase the solubility of the compound. Examples of carriers and excipients include calcium carbonate, calcium phosphate, various sugars or types of starch, cellulose derivatives, gelatin, vegetable oils, polyethylene glycols and physiologically compatible solvents and solutions.

The compositions can be administered by different routes including intravenously, intraperitoneally, subcutaneously, intramuscularly, orally, topically, or transmucosally. Pharmaceutical preparations for oral use can be obtained, for example by combining the active compounds with solid excipient, optionally grinding a resulting mixture, and processing the mixture of granules, after adding suitable auxiliaries, if desired, to obtain tablets or dragee cores. Suitable excipients include fillers such as sugars, including lactose, sucrose, mannitol, and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents may be added, such as the cross-linked polyvinyl pyrrolidone, agar, or alginic acid or a salt thereof such as sodium alginate.

Dragee cores should be provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

If desired, the composition can be administered at short time intervals using a pump to control the time interval or achieve continuously administration. Suitable pumps are commercially available (e.g., the ALZET® pump sold by Alza corporation, and the BARD ambulatory PCA pump sold by Bard MedSystems).

B. Dosage

The proper dosage depends on various factors such as the type of disease being treated, the particular composition being used, and the size and physiological condition of the patient. Therapeutically effective doses can be determined using standard techniques. For example, therapeutically effective doses for the compounds described herein can be estimated initially from cell culture and animal models. For example, a dose can be formulated in animal models to achieve a circulating concentration range that initially takes into account the $IC_{50}$ as determined in cell culture assays. The animal model data can be used to more accurately determine useful doses in humans.

Plasma half-life and biodistribution of the drug and metabolites in the plasma, tumors, and major organs can also be determined to facilitate the selection of drugs most appropriate to inhibit a disorder. Such measurements can be carried out, for example, using HPLC analysis from dissected animals treated with the drug. Compounds that show potent inhibitory activity in the screening assays, but have poor pharmacokinetic characteristics, can be optimized by altering the chemical structure and retesting. In this regard, compounds displaying good pharmacokinetic characteristics can be used as a model.

Toxicity studies can also be carried out by measuring the blood cell composition. For example, toxicity studies can be carried out as follows: 1) the compound is administered to mice (untreated control mice should also be used); 2) blood samples are periodically obtained via the tail vein from one mouse in each treatment group; and 3) the samples are analyzed for red and white blood cell counts, blood cell composition, and the percent of lymphocytes versus polymorphonuclear cells. A comparison of results for each dosing regime with the controls indicates if toxicity is present.

At the termination of each study, further studies can be carried out by sacrificing the animals (preferably, in accordance with the American Veterinary Medical Association guidelines Report of the American Veterinary Medical Assoc. Panel on Euthanasia, *Journal of American Veterinary Medical Assoc.*, 202:229–249, 1993). Representative animals from each treatment group can then be examined by gross necropsy for immediate evidence of metastasis, unusual illness, or toxicity. Gross abnormalities in tissue are noted, and tissues are examined histologically. Compounds causing a reduction in body weight or blood components are less preferred, as are compounds having an adverse effect on major organs. In general, the greater the adverse effect the less preferred the compound.

For the treatment of cancers the expected daily dose of a Structure I or II compound is between 1 to 2,000 mg/day, preferably 1 to 250 mg/day, and most preferably 1 to 150 mg/day. Drugs can be delivered less frequently provided plasma levels of the active moiety are sufficient to maintain therapeutic effectiveness.

A factor which can influence the drug dose is body weight.

Drugs should be administered at doses ranging from 0.02 to 25 mg/kg/day, preferably 0.02 to 15 mg/kg/day. Alternatively, drugs can be administered at 0.5 to 1200 mg/m²/day, preferably 0.5 to 150 mg/m²/day, most preferably 0.5 to 100 mg/m²/day. The average plasma level should be 50 to 5000 µg/ml, preferably 50 to 1000 µg/ml, and most preferably 10 to 500 µg/ml. Plasma levels may be reduced if pharmacological effective concentrations of the drug are achieved at the site of interest.

VI. Combination Treatment

The compounds described herein can be used alone or in combination with other types of treatment for hyperproliferative cell disorders. For example, various different types of general treatments are currently used to treat different types of cancer patients. See, Section IV supra.

VII. Examples

Examples are provided below to illustrate different aspects and embodiments of the present invention. These examples are not intended in any way to limit the disclosed invention. Rather, they illustrate methodology by which drugs having the disclosed formula can be readily identified by routine procedure to ensure that they have the desired activity. That is, compounds within the formula claimed herein can be screened to determine those with the most appropriate activity prior to administration to an animal or human. Other compounds can also be screened to determine suitability for use in methods of this invention.

EXAMPLE 1

In Vitro Tumor Inhibition

This example illustrates the ability of Structure I compounds to inhibit tumor growth using a growth assay. AA10, AA12 and AA14, were tested for their ability to inhibit anchorage-dependent tumor cell growth using the colorimetric assay described by Skehan et al., *J. Natl. Cancer Inst.*, 82:1107–1112, 1990. The assay measures protein content of acid-fixed cells using the counterion binding dye sulforhodamine B (SRB, Sigma).

AA10 and AA12 were solubilized in DMSO (Sigma, cell culture grade), and AA14 was dissolved in PBS (pH 7.4), the compounds were diluted into appropriate growth medium at two-fold the desired final assay concentration.

Compound (100 μL) was added to 96-well plates containing attached cellular monolayers C6 cells (2000 cells/ well in 100 μL). After 4 days (37° C., 5% $CO_2$) the monolayers were washed 3 times with PBS and fixed with 200 μL ice-cold 10% trichloroacetic acid (TCA) (Fisher Scientific), and kept at 4° C. for 60 minutes. The TCA was removed and the fixed monolayers were washed 5 times with tap water and allowed to dry completely at room temperature on absorbent paper. The cellular protein was stained for 10 min with 100 μL 0.4% SRB dissolved in 1% acetic acid. After 5 washes with tap water, the dye was solubilized in 10 mM Tris base (100 μL per well) and absorbance read at 570 nm on a Dynatech plate reader model MR5000. Growth inhibition data are expressed as a percentage of absorbance detected in control wells which were treated with 0.4% DMSO or PBS alone. DMSO and PBS controls were not different from cells grown in regular growth medium. $IC_{50}$ values were determined using a four parameter curve fit function.

The results of the growth assay are shown in Table II.

TABLE II

| Compound | $IC_{50}$ μM |
|---|---|
| AA10 | 2 |
| AA12 | 0.8 |
| AA14 | 0.8 |
| 3 | <1 |
| 6 | 31.2 |
| 7 | 36.7 |
| 12 | >100 |
| 17 | 15.2 |
| 22 | 24.3 |
| 27 | >20 |
| 32 | 35.3 |
| 37 | 6.1 |
| 42 | 53.3 |
| AA17 | 30 |
| AA18 | 24 |

EXAMPLE 2
In vivo Tumor Inhibition

In vivo tumor inhibition was measured using a subcutaneous Xenograft model. Mice (BALB/c, nu/nu) were implanted with C6 glioma cells and the ability of compounds AA10, AA12, and AA14 to inhibit tumor growth were measured.

C6 cells were maintained in Ham's F10 supplemented with 10% fetal bovine serum (FBS) and 2 mM glutamine (GLN). Cells were harvested at or near confluence with 0.05% Trypsin-EDTA and pelleted at 450×g for 10 min. Pellets were resuspended in sterile PBS or media (without FBS) to a particular concentration and the cells were implanted into the hindflank of mice. Tumor growth was measured over 3 to 6 weeks using venier calipers. Tumor volumes were calculated as a product of length×width× height unless otherwise indicated. AA10 and AA12 were solubilized in 50–100 μL vehicle (DMSO) while AA14 was dissolved in PBS (pH 7.4). The compounds were delivered by IP injection at 15 mg/kg/day.

Figure 2:
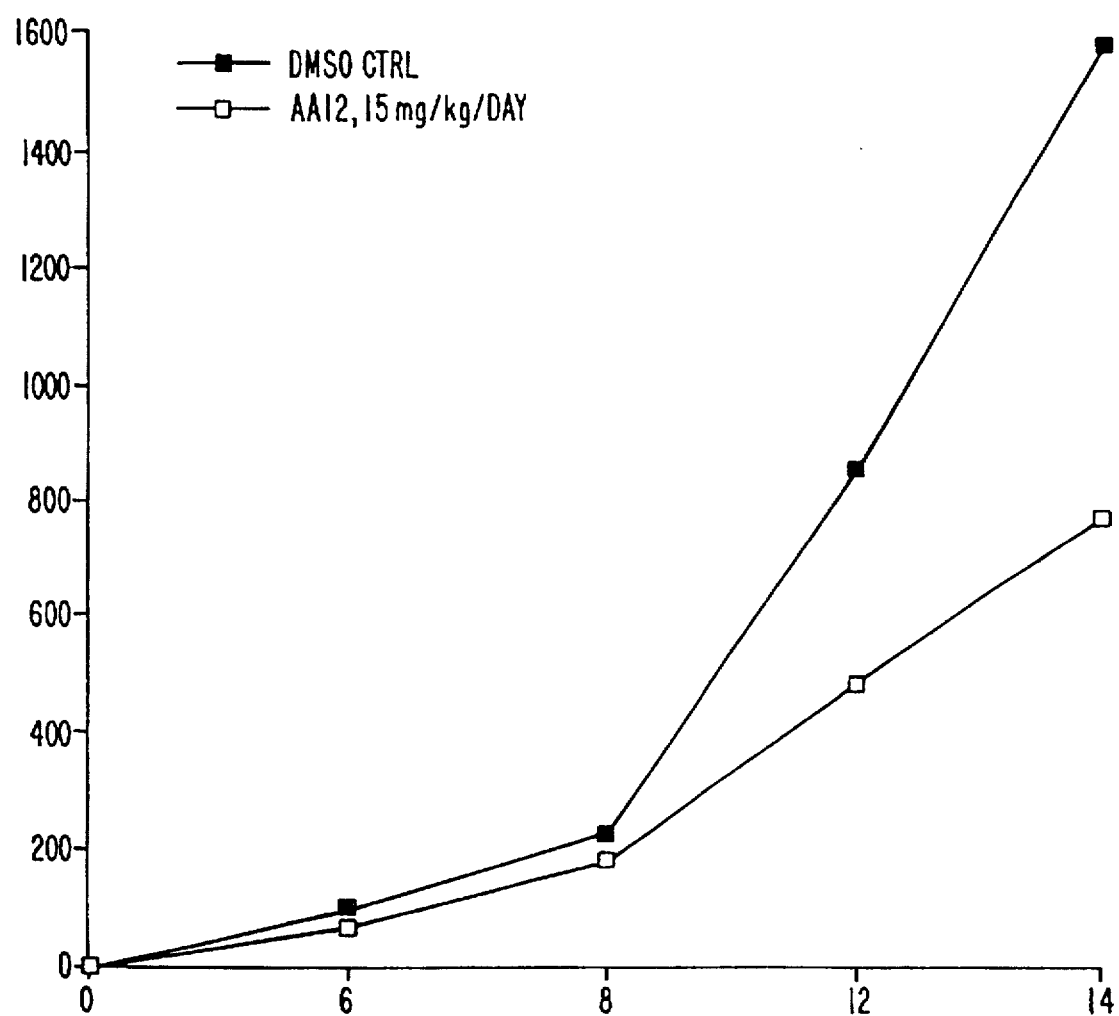
FIG. 2 illustrates the ability of AA12 to inhibit glioma cells in a Xenograft model.
Figure 3:
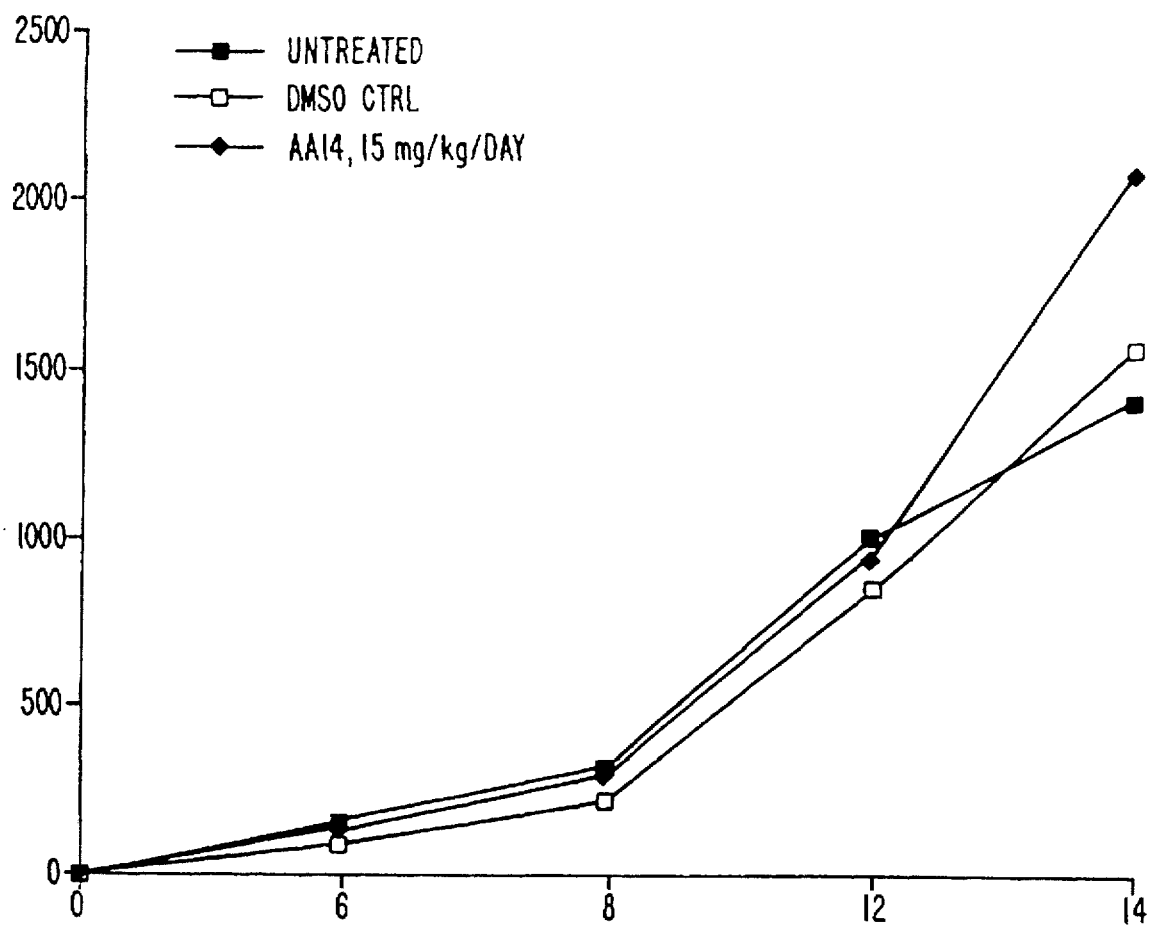
FIG. 3 illustrates the ability of AA14 to inhibit glioma cells in a Xenograft model.

FIGS. 1, 2, and 3 graphically illustrate the ability of compounds AA10, AA12, and AA14, respectively, to inhibit tumor growth. Increased efficacy can be obtained by optimizing dosing regiments. For example, the amount and timing of the doses can be varied and tested using procedures known in the art and described herein.

EXAMPLE 3
Effects of Higher AA14 concentrations

Figure 4:
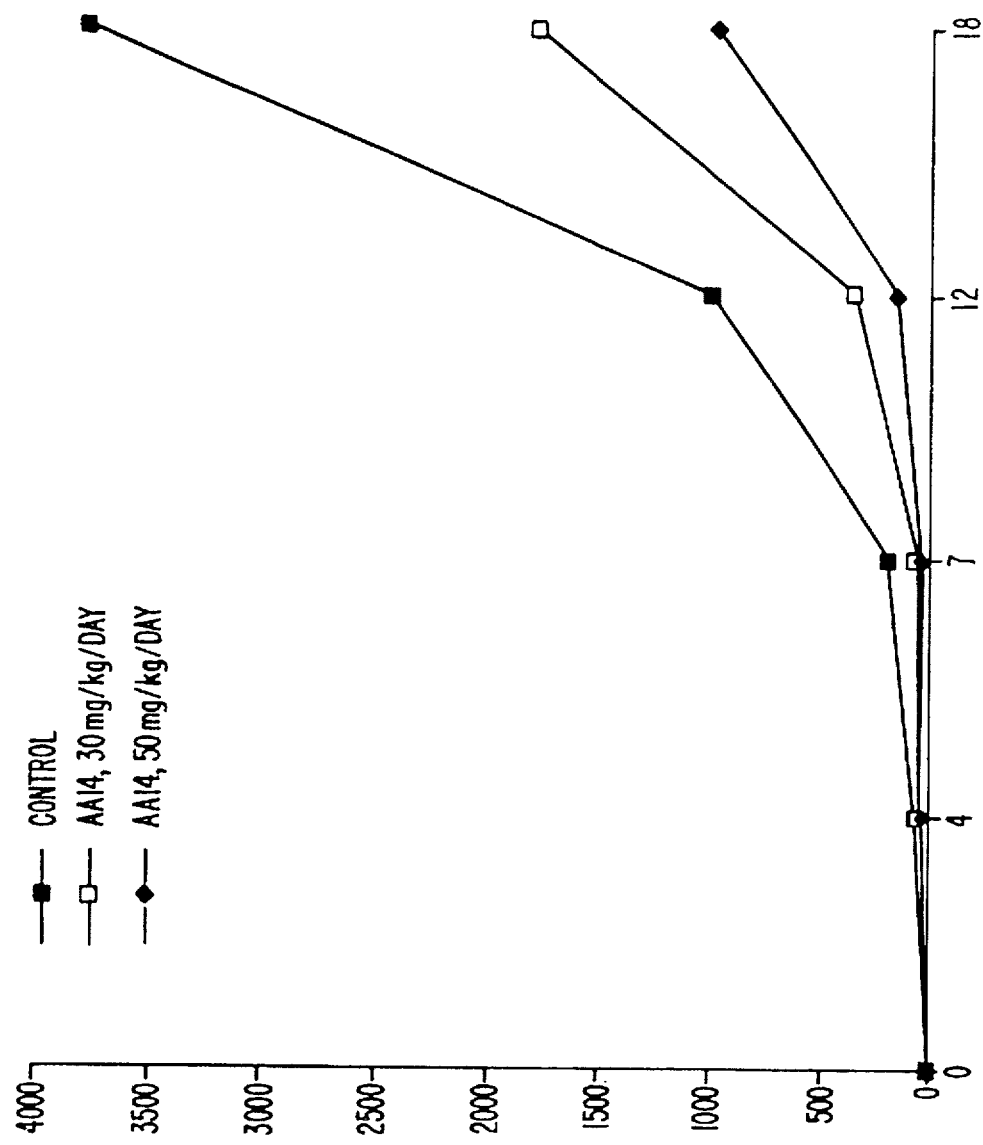
FIG. 4 illustrates the ability of higher concentrations of AA14 to inhibit glioma cells in a Xenograft model.

This example illustrates the effects of higher AA14 concentrations. The effects of higher concentrations of AA14 on mice were determined using the protocol described in Example 2. The compound was dissolved in phosphate buffered saline and the animals were treated with 30 mg/kg/ day and 50 mg/kg/day. The results are shown in FIG. 4. The higher amounts of drug resulted in increased tumor inhibition.

EXAMPLE 4
Toxicity Studies

Toxicity studies were carried out in animal models for AA10, AA12 and AA14. AA10 and AA12 were solubilized in DMSO and AA14 was dissolved in PBS (pH 7.4). The dosage resulting in a 50% mortality rate ($LD_{50}$) and a 10% mortality rate ($LD_{10}$) was determined as described below.

Five mice (BALB/c) were treated with different concentrations of compound. All animals were observed for 7 to 14 days after the last dose was administered. The $LD_{50}$ was calculated from a plot of % mortality versus dose (log M) using a four parameter logistic equation.

Table III illustrates the results of the different studies using different compounds.

TABLE III

| Toxicity Studies | | |
|---|---|---|
| Compound | $LD_{50}$ (mg/kg) | $LD_{10}$ (mg/kg) |
| AA10 | 96 | 77 |
| AA12 | 79 | 62 |
| AA14 | 145 | 120 |

At the end of the experiment an animal from each study administered with 100 mg/kg of compound was sacrificed and pathologically analyzed for organ damage. No significant toxicity was observed.

EXAMPLE 5
Synthesis of AA10: 5-Methyl-4-(4-trifluoromethylphenyl) aminothiocarbonylisoxazole

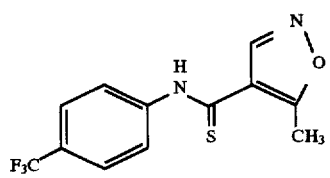

A solution of 24 grams of 5-methyl-4-(4-trifluoromethylphenyl)aminocarbonylisoxazole and 39 grams of Lawesson's reagent [2,4-bis(4-methoxyphenyl)-1, 3-dithia-2,4-diphosphetane-2,4-disulfide] in 400 ml of toluene was refluxed for three hours. Upon cooling of mixture to room temperature, all the solid was filtered off and the filtrate was concentrated. The resulting crude product from the filtrate was then purified on a silica gel column with 3% methanol in dichloromethane to yield 16.5 grams of 5-methyl-4-(4-trifluoromethylphenyl) aminothiocarbonylisoxazole.

EXAMPLE 6

Synthesis of AA11: 4-(4-Chlorophenylsulfonyl)-5-methylisoxazole

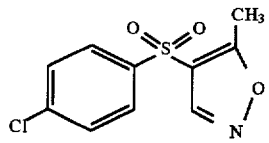

A 10 gram suspension of 2-(4-chlorophenylsulfonyl)-1-ethoxypropene in 30 ml of ethanol was added with a solution of 1.1 equivalent of hydroxylamine in 20 ml of water. The mixture was then stirred at room temperature for 2 hours, chilled in an ice-water bath for 30 minutes and filtered. The resulting solid was crystallized in ethanol and water to provide 8.0 grams of 4-(4-chlorophenylsulfonyl)-5-methylisoxazole.

EXAMPLE 7

Synthesis of AA12: 1-Cyano-2-hydroxy-1-(4-trifluoromethylphenyl)aminothiocarbonylpropene

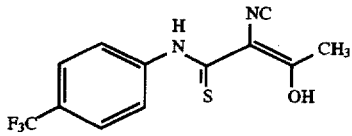

A solution of 7.0 grams of 5-methyl-4-(4-trifluoromethylphenyl)aminothiocarbonylisoxazole and 5 ml of 1,8-diazabicyclo[5.4.0]undec-7-ene in 50 ml of ethanol was heated at 80° C. for 8 hours. The reaction mixture was cooled to room temperature and acidified with 6N hydrochloric acid solution until pH 2. The mixture was then cooled in an ice-water bath for 30 minutes and the solid was filtered, washed with a chilled solution of ethanol and water (2:1) and dried by suction to provide 5.0 grams of 1-cyano-2-hydroxy-1-(4-trifluoromethylphenyl) aminothiocarbonylpropene.

Alternatively, AA12 can be prepared by reacting 4-trifluoromethylisothiocyanoate and 1-sodio-1-cyano acetone in tetrafuran followed by acidification.

EXAMPLE 8

Synthesis of AA13: 1-(4-chlorophenylsulfonyl)-1-cyano-2-hydroxypropene

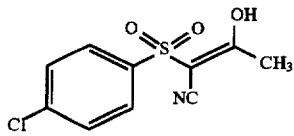

AA13 was prepared starting with AA11 using the same conditions as described for AA12.

EXAMPLE 9

Synthesis of AA14: 1-Cyano-2-hydroxy-1-(4-trifluoromethylphenylaminothiocarbonyl)propene sodium salt

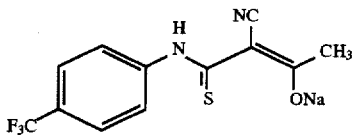

A mixture of 2.8 grams of 5-methyl-4-(4-trifluoromethylphenyl)aminothiocarbonylisoxazole and 400 mg of sodium hydroxide in 25 ml of ethanol and 10 ml of water was heated at 70° C. for 6 hours. All the ethanol was removed and the resulting solution was lyophilized to give 2 grams of 1-cyano-2-hydroxy-1-(4-trifluoromethylphenylaminothiocarbonyl)propene sodium salt.

Alternatively AA14 can be prepared by mixing AA12 with equimolar amounts of sodium hydroxide in ethanol and water followed by lyophilization.

EXAMPLE 10

Synthesis of AA15: 1-(4-Chlorophenylsulfonyl)-1-cyano-2-hydroxypropene sodium salt

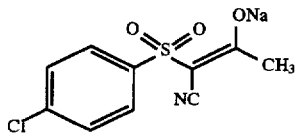

AA15 was prepared from AA11 or AA13 using similar conditions as described for AA14.

EXAMPLE 11

Synthesis of AA16: 4-(4-Trifluoromethylphenylaminosulfonyl)-5-methylisoxazole

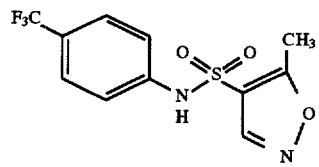

AA16 was prepared starting from 2-(4-trifluoromethylphenylaminosulfonyl)1-ethoxypropene under the same conditions as described for AA11. Alternatively, AA16 was prepared from 4-trifluoromethylaniline and 4-chlorosulfonyl-5-methylisoxazole.

EXAMPLE 12

Synthesis of AA17: 1-Cyano-2-hydroxy-1-(4-trifluoromethylphenylaminosulfonyl)propene

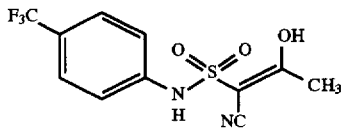

AA17 was prepared starting from AA16 using similar conditions as described for AA12.

Alternatively, AA17 can be prepared from the sodium salt of N-3-trifluoromethylphenyl cyanomethyl sulfonamide with acetyl chloride.

EXAMPLE 13

Synthesis of AA18: 1-cyano-2-hydroxy-1-(4-trifluoromethylphenylaminosulfonyl)propene sodium salt

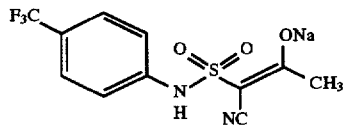

AA18 was prepared from either AA16 or AA17 using similar conditions as described for AA14.

EXAMPLE 14
Alternative Synthesis of Compound AA12

Sodium hydroxide (6.5 g) and 13.5 ml of water were charged to a 200 ml two neck flask equipped with a condenser and a stirrer. Ethanol (60 ml) was added after the sodium hydroxide was completely dissolved. 5-Methylisoxazole (14.5 ml) was added dropwise over 1 hour. The reaction mixture was stirred for 7 hours at room temperature. 4-(Trifluoromethyl)phenylisothiocyanate (30.0 g) was added portion wise as a solid and stirred at room temperature for 12 hours. TLC (5% methanol in ethylacetate) showed that no 4-(trifluoromethyl) phenylisothiocyanate remained. The reaction mixture was decolorized by adding activated carbon (2.0 g) and stirring for 1 hour. The reaction mixture was filtered through celite 521 and the solids washed with 90 ml of 2:1 ethanol:water. The filtrate was stirred, 40 ml of 4N hydrochloric acid was added and the pH of the solution adjusted to 1–2. The solids were collected by vacuum filtration and washed with 60 ml of 2:1 ethanol:water. The solids were dried under vacuum at 40° C. for 8–10 hours. To decolorize the product, 38.0 g of the dried solids were suspended in 228 mL of ethanol and heated at 60° C. for 2 hours. The mixture was cooled at 0°–5° C. for 4 hours. The light yellow solid was collected by vacuum filtration, washed with 60 mL of cold ethanol and dried in a vacuum oven at 40° C. for 14 hours. The yield of 3-hydroxy-3-methyl-2-[(4-trifluoromethylphenyl) aminothiocarbonyl]acrylonitrile was 36.0 g (85%).

EXAMPLE 15
Alternative Synthesis of Compound AA14

3-Hydroxy-3-methyl-2-[(4-trifluoromethylphenyl) aminothiocarbonyl] acrylonitrile (50.0 g) and 175.0 mL of DI water were charged to a 500 mL flask equipped with a stirrer. Sodium hydroxide (6.98 g) was dissolved in 175.0 mL DI water and added to the suspended material. Stirring was continued until the (E)-3-hydroxy-3-methyl-2-[(4-trifluoromethylphenyl)aminothiocarbonyl]acrylonitrile dissolved. The solution was filtered under vacuum and freeze dried to give 48.0 g of the sodium salt of 3-hydroxy-3-methyl-2-[[4-(trifluoromethyl)phenyl]aminothiocarbonyl] acrylonitrile sodium salt in 89% yield.

EXAMPLE 16

Synthesis of 3-cyclopropyl-3-hydroxy-2-[(4-trifluoromethylphenyl) aminothiocarbonylacrylonitrile, Compound 3

A sample of 3-hydroxy-3-methyl-2-[(4-trifluoromethylphenyl)aminothiocarbonyl]acrylonitrile (10 g) was heated in a mixture of tetrahydrofuran (30 ml) and 1N hydrochloric acid (15 ml) at 80° C. for 8 hrs. The mixture was diluted with 100 ml of water and extracted with 2×100 ml of ethyl acetate. The organic extracts were washed with saturated sodium bicarbonate solution, brine, dried over sodium sulfate and filtered. After concentration of the filtrate, the crude was eluted on a silica gel column with ethyl acetate as the elutant to provide 3.5 g of 4-trifluoromethylphenyl cyanothioacetamide as a red solid with a mp of 89.5° C. $^1$H NMR (360 MHz, DMSO): δ2.5 (5.3 H), 4.3 (5.2 H), 7.80 (d, 2H, J=9 Hz) 8.04 (d, 2H, J=9 Hz) 12.14 (5.1 H).

To a suspension of 500 mg of sodium hydride (60% oil suspension) in 3 ml of acetonitrile in a ice-water bath was combined with 900 mg of 4-trifluoromethylphenyl cyanothioacetamide in 7 ml of tetrahydrofuran dropwise. After stirring for 30 minutes, the resulting suspension was chilled at –20° C. and was combined with 400 mg of cyclopropane carbonyl chloride. The reaction mixture was stirred at –20° C. for 30 minutes, warmed up to room temperature and stirred for another 45 minutes. The crude extract was diluted with 50 ml of water, acidified with 1N hydrochloric acid solution and extracted with 2×50 ml of ethyl acetate. The combined organic extracts were washed with brine, dried over sodium sulfate, filtered and concentrated. After concentration of the filtrate, the crude was eluted on a silica gel column with ethyl acetate as the elutant to provide 150 mg of 3-cyclopropyl-3-hydroxy-2-[(4-trifluoromethylphenyl) aminothio-carbonyl]acrylonitrile.

EXAMPLE 17
Synthesis of Compounds 4–6

Compound 4 (3-hydroxy-3-allyl-2-[[4-(trifluoromethyl) phenyl]amino-thiocarbonyl]acrylonitrile), and Compound 6 (3-hydroxy-3-(propen-2-yl)-2-[[4-(trifluoro-methyl)phenyl] aminothiocarbonyl]acrylonitrile) were prepared following the synthesis protocol as described in Example 16 using the appropriate starting reagent. Compound 5 (3-hydroxy-3-isopropyl-2-[[4-(trifluoromethyl)-phenyl]amino-thiocarbonyl]-acrylonitrile), can be prepared in a similar manner.

EXAMPLE 18
Synthesis of Compounds 7–11

Compound 7 (3-hydroxy-3-methyl-2-[(2-bromo-4-fluorophenyl)aminothiocarbonyl]acrylonitrile) was prepared following the synthesis protocol as described in Examples 14 and 16 starting from 2-bromo-4-fluorophenylisothiocyanate. Compound 8 (3-hydroxy-3-cyclopropyl-2-[(2-bromo-4-fluorophenyl) aminothiocarbonyl]acrylonitrile), Compound 9 (3-hydroxy- 3-allyl-2-[(2-bromo-4-fluorophenyl)-aminothiocarbonyl]-acrylonitrile), Compound 10 (3-hydroxy-3-isopropyl-2-[(2-bromo-4-fluorophenyl)aminothiocarbonyl]acrylonitrile) and Compound 11: 3-hydroxy-3-(propen-2-yl)-2-[(2-bromo-4-fluorophenyl)aminothiocarbonyl]acrylonitrile can be prepared in a similar manner.

EXAMPLE 19
Synthesis of Compounds 12–16

Compound 12 (3-hydroxy-3-methyl-2-[[2-(trifluoromethyl)phenyl]aminothiocarbonyl]acrylonitrile) was prepared following the synthesis protocol described in Examples 14 and 16 starting from 2-trifluoromethylphenylisothiocyanate. Compound 13 (3-hydroxy-3-cyclopropyl-2-[[2-(trifluoromethyl)-phenyl] aminothiocarbonyl]acrylonitrile), Compound 14 (3-hydroxy-3-allyl-2-[[2-(trifluoromethyl)-phenyl] aminothiocarbonyl]acrylonitrile, Compound 15 (3-hydroxy-3-isopropyl-2-[[2-(trifluoromethyl)-phenyl] aminothiocarbonyl]acrylonitrile), and Compound 16 (3-hydroxy-3-(propen-2-yl)-2-[[2-(trifluoromethyl)phenyl] aminothiocarbonyl]-acrylonitrile) can be prepared in a similar manner.

EXAMPLE 20
Synthesis of Compounds 17–21

Compound 17 (3-hydroxy-3-methyl-2-[[3-(trifluoromethyl)phenyl]aminothiocarbonyl]acrylonitrile) was prepared following the synthesis protocol described in Examples 14 and 16 starting from 3-trifluoromethylphenylisothiocyanate. Compound 18 (3-hydroxy-3-cyclopropyl-2-[[3-(trifluoromethyl)-phenyl] aminothiocarbonyl]acrylonitrile), Compound 19 (3-hydroxy-3-allyl-2-[[3-(trifluoromethyl)-phenyl] aminothiocarbonyl]acrylonitrile), Compound 20 (3-hydroxy-3-isopropyl-2-[[3-(trifluoromethyl)-phenyl] aminothiocarbonyl]acrylonitrile), and Compound 21 (3-hydroxy-3-(propen-2-yl)-2-[[3-(trifluoromethyl)-phenyl] amino-thiocarbonyl]acrylonitrile) can be prepared in a similar manner.

EXAMPLE 21
Synthesis of Compounds 22–26

Compound 22 (3-hydroxy-3-methyl-2-[[4-(piperidine-1-sulfonyl)-phenyl]aminothiocarbonyl]acrylonitrile) was prepared following the synthesis protocol described in Examples 14 and 16 starting from 4-(piperidine-1-sulfonyl) phenylisothiocyanate. Compound 23 (3-hydroxy-3-cyclopropyl-2-[[4-(piperidine-1-sulfonyl)phenyl]aminothiocarbonyl]acrylonitrile), Compound 24 (3-hydroxy-3-allyl-2-[[4-(piperidine-1-sulfonyl)phenyl]-aminothiocarbonyl]acrylonitrile), Compound 25 (3-hydroxy-3-isopropyl-2-[[4-(piperidine-1-sulfonyl) phenyl]amino thiocarbonyl]acrylonitrile), and Compound 26 (3-hydroxy-3-(propen-2-yl)-2-[[4-(piperidine-1-sulfonyl)phenyl]amino-thiocarbonyl]acrylonitrile can be prepared in a similar manner.

EXAMPLE 22
Synthesis of Compounds 27–31

Compound 27 (3-hydroxy-3-methyl-2-[[4-(aminosulfonyl)phenyl]aminothiocarbonyl]acrylonitrile) was prepared following the synthesis protocol described in Examples 14 and 16 starting from 4-aminosulfonylphenylisothiocyanate. Compound 28 (3-hydroxy-3-cyclopropyl-2-[[4-(aminosulfonyl)-phenyl] aminothiocarbonyl]acrylonitrile), Compound 29 (3-hydroxy-3-allyl-2-[[4-(aminosulfonyl)-phenyl] aminothiocarbonyl]acrylonitrile, Compound, 30 (3-hydroxy-3-isopropyl-2-[[4-(aminosulfonyl)phenyl] aminothiocarbonyl]acrylonitrile), and Compound 31 (3-hydroxy-3-(2-propen-yl)-2-[[4-(aminosulfonyl)-phenyl] aminothiocarbonyl]acrylonitrile) can be prepared in a similar manner.

EXAMPLE 23
Synthesis of Compounds 32–36

Compound 32 (3-hydroxy-3-methyl-2-[(2,3-dichlorophenyl)aminothiocarbonyl]acrylonitrile) was prepared following the synthesis protocol described in Examples 14 and 16 starting from 2,3-dichlorophenylisothiocyanate. Compound 33 (3-hydroxy-3-cyclopropyl-2-[(2,3-dichlorophenyl)-aminothiocarbonyl]-acrylonitrile), Compound 34 (3-hydroxy-3-allyl-2-[(2,3-dichlorophenyl)-aminothiocarbonyl]acrylonitrile), Compound 35 (3-hydroxy-3-isopropyl-2-[(2,3-dichlorophenyl)]-aminothiocarbonyl]acrylonitrile), and Compound 36 (3-hydroxy-3-(propen-2-yl)-2-[(2,3-dichlorophenyl)-aminothiocarbonyl]-acrylonitrile) can be prepared in a similar manner.

EXAMPLE 24
Synthesis of Compounds 37–41

Compound 37 (3-hydroxy-3-methyl-2-[(3,4-dichlorophenyl)aminothiocarbonyl]acrylonitrile) was prepared following the synthesis protocol described in Examples 14 and 16 starting from 3,4-dichlorophenylisothiocyanate. Compound 38 (3-hydroxy-3-cyclopropyl-2-[(3,4-dichlorophenyl)-aminothiocarbonyl] acrylonitrile), Compound 39 (3-hydroxy-3-allyl-2-[(3,4-dichlorophenyl)-aminothiocarbonyl]acrylonitrile), Compound 40 (3-hydroxy-3-isopropyl-2-[(3,4-dichlorophenyl)aminothio-carbonyl]acrylonitrile), and Compound 41 (3-hydroxy-3-(propen-2-yl)-2-[(3,4-dichlorophenyl)-aminothiocarbonyl]-acrylonitrile can be prepared in a similar manner.

EXAMPLE 25
Synthesis of Compounds 42–46

Compounds 42–46 can be produced using standard techniques, for example, by using the synthesis protocol described in Examples 14 and 16 starting from 2-4-dichlorophenylisothiocyanate. Compounds 42–46 are as follows:

Compound 42: 3-hydroxy-3-methyl-2-[(2,4-dichlorophenyl)aminothiocarbonyl]acrylonitrile;

Compound 43: 3-hydroxy-3-cyclopropyl-2-[(2,4-dichlorophenyl)aminothiocarbonyl]acrylonitrile;

Compound 44: 3-hydroxy-3-allyl-2-[(2,4-dichlorophenyl)aminothiocarbonyl]acrylonitrile;

Compound 45: 3-hydroxy-3-isopropyl-2-[(2,4-dichlorophenyl)aminothiocarbonyl]acrylonitrile; and Compound 46: 3-hydroxy-3-(propen-2-yl)-2-[(2,4-dichlorophenyl)aminothiocarbonyl]acrylonitrile.

EXAMPLE 26
Synthesis of Compounds 47–51

Compounds 47–51 can be produced using standard techniques, for example, by using the synthesis protocol described in Examples 14 and 16 starting from 4-trifluoromethoxyphenylisothiocyanate. Compounds 47–51 are as follows:

Compound 47: 3-hydroxy-3-methyl-[[4-(trifluoromethoxy)phenyl]aminothiocarbonyl] acrylonitrile;

Compound 48: 3-hydroxy-3-cyclopropyl-[[4-(trifluoromethoxy)phenyl]aminothiocarbonyl]acrylonitrile;

Compound 49: 3-hydroxy-3-allyl-[[4-(trifluoromethoxy)phenyl]aminothiocarbonyl]acrylonitrile;

Compound 50: 3-hydroxy-3-isopropyl-[[4-(trifluoromethoxy)phenyl]aminothiocarbonyl]acrylonitrile; and Compound 51: 3-hydroxy-3-(propen-2-yl)-[[4-(trifluoromethoxy)phenyl]aminothiocarbonyl]acrylonitrile.

EXAMPLE 27
Synthesis of Compounds 52–56

Compounds 52–56 can be produced using standard techniques, for example, by using the synthesis protocol described in Examples 14 and 16 starting from 3,5-di-trifluoromethylphenylisothiocyanate.

Compounds 52–56 are as follows:

Compound 52: 3-hydroxy-3-methyl-[[3,5-di-(trifluoromethyl)phenyl]aminothiocarbonyl]acrylonitrile;

Compound 53: 3-hydroxy-3-cyclopropyl-[[3,5-di-(trifluoromethyl)phenyl]aminothiocarbonyl]acrylonitrile;

Compound 54: 3-hydroxy-3-allyl-[[3,5-di-(trifluoromethyl)phenyl]aminothiocarbonyl]acrylonitrile;

Compound 55: 3-hydroxy-3-isopropyl-[[3,5-di-(trifluoromethyl)phenyl]aminothiocarbonyl]acrylonitrile; and Compound 56: 3-hydroxy-3-(propen-2-yl)-[[3,5-di-(trifluoromethyl)-phenyl]amino thiocarbonyl]acrylonitrile.

EXAMPLE 28
Synthesis of Compounds 57–61

Compounds 57–61 can be produced using standard techniques, for example, by using the synthesis protocol described in Examples 14 and 16 starting from 2-fluorophenylisothiocyanate. Compounds 57–61 are as follows:

Compound 57: 3-hydroxy-3-methyl-2-[(2-fluorophenyl)aminothiocarbonyl]acrylonitrile;

Compound 58: 3-hydroxy-3-cyclopropyl-2-[(2-fluorophenyl)aminothiocarbonyl]acrylonitrile;

Compound 59: 3-hydroxy-3-allyl-2-[(2-fluorophenyl)aminothiocarbonyl]acrylonitrile;

Compound 60: 3-hydroxy-3-isopropyl-2-[(2-fluorophenyl)aminothiocarbonyl]acrylonitrile; and Compound 61: 3-hydroxy-3-(propen-2-yl)-2-[(2-fluorophenyl)aminothiocarbonyl]acrylonitrile.

EXAMPLE 29
Synthesis of Compounds 62–66

Compounds 62–66 can be produced using standard techniques, for example, by using the synthesis protocol described in Examples 14 and 16 starting from 2,4-difluorophenylisothiocyanate. Compounds 61–66 are as follows:

Compound 62: 3-hydroxy-3-methyl-2-[(2,4-difluorophenyl)aminothiocarbonyl]acrylonitrile;

Compound 63: 3-hydroxy-3-cyclopropyl-2-[(2,4-difluorophenyl)aminothiocarbonyl]acrylonitrile;

Compound 64: 3-hydroxy-3-allyl-2-[(2,4-difluorophenyl)aminothiocarbonyl]acrylonitrile;

Compound 65: 3-hydroxy-3-isopropyl-2-[(2,4-difluorophenyl)aminothiocarbonyl]acrylonitrile; and Compound 66: 3-hydroxy-3-(propen-2-yl)-2-[(2,4-difluorophenyl)aminothiocarbonyl]acrylonitrile.

EXAMPLE 30
Synthesis of Compounds 67–71

Compounds 67–71 can be produced using standard techniques, for example, by using the synthesis protocol described in Examples 14 and 16 starting from 2,6-difluorophenylisothiocyanate. Compounds 67–71 are as follows:

Compound 67: 3-hydroxy-3-methyl-2-[(2,6-difluorophenyl)aminothiocarbonyl]acrylonitrile;

Compound 68: 3-hydroxy-3-cyclopropyl-2-[(2,6-difluorophenyl)aminothiocarbonyl]acrylonitrile;

Compound 69: 3-hydroxy-3-allyl-2-[(2,6-difluorophenyl)aminothiocarbonyl]acrylonitrile;

Compound 70: 3-hydroxy-3-isopropyl-2-[(2,6-difluorophenyl)aminothiocarbonyl]acrylonitrile; and Compound 71: 3-hydroxy-3-(propen-2-yl)-2-[(2,6-difluorophenyl)aminothiocarbonyl]acrylonitrile.

EXAMPLE 31
Synthesis of Compounds 72–76

Compounds 72–76 can be produced using standard techniques, for example, by using the synthesis protocol described in Examples 14 and 16 starting from 2,4,6-trifluorophenylisothiocyanate. Compound 72–76 are as follows:

Compound 72: 3-hydroxy-3-methyl-2-[(2,4,6-trifluorophenyl)aminothiocarbonyl]acrylonitrile;

Compound 73: 3-hydroxy-3-cyclopropyl-2-[(2,4,6-trifluorophenyl)aminothiocarbonyl]acrylonitrile;

Compound 74: 3-hydroxy-3-allyl-2-[(2,4,6-trifluorophenyl)aminothiocarbonyl]acrylonitrile;

Compound 75: 3-hydroxy-3-isopropyl-2-[(2,4,6-trifluorophenyl)aminothiocarbonyl]acrylonitrile; and Compound 76: 3-hydroxy-3-(propen-2-yl)-2-[(2,4,6-trifluorophenyl)-aminothiocarbonyl]acrylonitrile.

EXAMPLE 32
Synthesis of Compounds 77–81

Compounds 77–81 can be produced using standard techniques, for example, by using the synthesis protocol described in Examples 14 and 16 starting from 2-chloro-3-trifluoromethylphenylisothiocyanate. Compounds 77–81 are as follows:

Compound 77: 3-hydroxy-3-methyl-2-[[(2-chloro-3-(trifluoromethyl)-phenyl]aminothiocarbonyl]acrylonitrile, Compound 78: 3-hydroxy-3-cyclopropyl-2-[[(2-chloro-3-(trifluoromethyl)phenyl]aminothiocarbonyl]acrylonitrile;

Compound 79: 3-hydroxy-3-allyl-2-[[(2-chloro-3-(trifluoromethyl)-phenyl]aminothiocarbonyl]acrylonitrile;

Compound 80: 3-hydroxy-3-isopropyl-2-[[(2-chloro-3-(trifluoromethyl)-phenyl]aminothiocarbonyl]acrylonitrile; and Compound 81: 3-hydroxy-3-(propen-2-yl)-2-[[(2-chloro-3-(trifluoromethyl)phenyl]aminothiocarbonyl]acrylonitrile.

EXAMPLE 33
Synthesis of Compounds 82–86

Compounds 82–86 can be produced using standard techniques, for example, by using the synthesis protocol described in Examples 14 and 16 starting from 4-bromo-2-trifluoromethylphenylisothiocyanate. Compounds 82–86 are as follows:

- Compound 82: 3-hydroxy-3-methyl-2-[[(4-bromo-2-(trifluoromethyl)-phenyl]aminothiocarbonyl] acrylonitrile;
- Compound 83: 3-hydroxy-3-cyclopropyl-2-[[(4-bromo-2-(trifluoromethyl)phenyl]aminothiocarbonyl] acrylonitrile;
- Compound 84: 3-hydroxy-3-allyl-2-[[(4-bromo-2-(trifluoromethyl)phenyl]aminothiocarbonyl] acrylonitrile;
- Compound 85: 3-hydroxy-3-isopropyl-2-[[(4-bromo-2-(trifluoromethyl)phenyl]aminothiocarbonyl] acrylonitrile; and
- Compound 86: 3-hydroxy-3-(propen-2-yl)-2-[[(4-bromo-2-(trifluoromethyl)phenyl]aminothiocarbonyl] acrylonitrile.

EXAMPLE 34
Synthesis of Compounds 87–91

Compounds 87–91 can be produced using standard techniques, for example, by using the synthesis protocol described in Examples 14 and 16 starting from 4-chloro-3-trifluoromethylphenyl-isothiocyanate. Compounds 87–91 are as follows:

- Compound 87: 3-hydroxy-3-methyl-2-[[(4-chloro-3-(trifluoromethyl)phenyl]aminothiocarbonyl] acrylonitrile;
- Compound 88: 3-hydroxy-3-cyclopropyl-2-[[(4-chloro-3-(trifluoromethyl)phenyl]aminothiocarbonyl] acrylonitrile;
- Compound 89: 3-hydroxy-3-allyl-2-[[(4-chloro-3-(trifluoromethyl)-phenyl]aminothiocarbonyl] acrylonitrile;
- Compound 90: 3-hydroxy-3-isopropyl-2-[[(4-chloro-3-(trifluoromethyl)phenyl]aminothiocarbonyl] acrylonitrile; and
- Compound 91: 3-hydroxy-3-(propen-2-yl)-2-[[(4-chloro-3-(trifluoromethyl)phenyl]aminothiocarbonyl] acrylonitrile.

EXAMPLE 35
Synthesis of Compounds 92–96

Compounds 92–96 can be produced using standard techniques, for example, by using the synthesis protocol described in Examples 14 and 16 starting from 2-cyano-3-fluorophenylisothiocyanate. Compounds 92–96 are as follows:

- Compound 92: 3-hydroxy-3-methyl-2-[(2-cyano-3-fluorophenyl)aminothiocarbonyl]acrylonitrile;
- Compound 93: 3-hydroxy-3-cyclopropyl-2-[(2-cyano-3-fluorophenyl)-aminothiocarbonyl]acrylonitrile;
- Compound 94: 3-hydroxy-3-allyl-2-[(2-cyano-3-fluorophenyl)-aminothiocarbonyl]acrylonitrile;
- Compound 95: 3-hydroxy-3-isopropyl-2-[(2-cyano-3-fluorophenyl)-aminothiocarbonyl]acrylonitrile; and
- Compound 96: 3-hydroxy-3-(propen-2-yl)-2-[(2-cyano-3-fluorophenyl)-aminothiocarbonyl]acrylonitrile.

EXAMPLE 36
Synthesis of Compounds 97–101

Compounds 97–101 can be produced using standard techniques, for example, by using the synthesis protocol described in Examples 14 and 16 starting from 3,4-difluorophenylisothiocyanate. Compounds 97–101 are as follows:

- Compound 97: 3-hydroxy-3-methyl-2-[(3,4-difluorophenyl)aminothiocarbonyl]acrylonitrile;
- Compound 98: 3-hydroxy-3-cyclopropyl-2-[(3,4-difluorophenyl)aminothiocarbonyl]acrylonitrile;
- Compound 99: 3-hydroxy-3-allyl-2-[(3,4-difluorophenyl)aminothiocarbonyl]acrylonitrile;
- Compound 100: 3-hydroxy-3-isopropyl-2-[(3,4-difluorophenyl)aminothiocarbonyl]acrylonitrile; and
- Compound 101: 3-hydroxy-3-(propen-2-yl)-2-[(3,4-difluorophenyl)aminothiocarbonyl]acrylonitrile.

EXAMPLE 37
Synthesis of Compounds 102–106

Compounds 102–106 can be produced using standard techniques, for example, by using the synthesis protocol described in Examples 14 and 16 starting from 5-trifluoromethylpyridine-2-isothiocyanate. Compounds 102–106 are as-follows:

- Compound 102: 3-hydroxy-3-methyl-2-[[5-(trifluoromethyl)pyrid-2-yl]aminothiocarbonyl] acrylonitrile;
- Compound 103: 3-hydroxy-3-cyclopropyl-2-[[5-(trifluoromethyl)pyrid-2-yl]aminothiocarbonyl] acrylonitrile;
- Compound 104: 3-hydroxy-3-allyl-2-[[5-(trifluoromethyl)pyrid-2-yl]aminothiocarbonyl] acrylonitrile;
- Compound 105: 3-hydroxy-3-isopropyl-2-[[5-(trifluoromethyl)pyrid-2-yl]aminothiocarbonyl] acrylonitrile; and
- Compound 106: 3-hydroxy-3-(propen-2-yl)-2-[[5-(trifluoromethyl)pyrid-2-yl]aminothiocarbonyl] acrylonitrile.

EXAMPLE 38
Synthesis of Compounds 107–111

Compounds 107–111 can be produced using standard techniques, for example, by using the synthesis protocol described in Examples 14 and 16 starting from 5-cyanopyridine-2-isothiocyanate. Compounds 107–111 are as follows:

- Compound 107: 3-hydroxy-3-methyl-2-[(5-cyanopyrid-2-yl)aminothiocarbonyl]acrylonitrile;
- Compound 108: 3-hydroxy-3-cyclopropyl-2-[(5-cyanopyrid-2-yl)aminothiocarbonyl]acrylonitrile;
- Compound 109: 3-hydroxy-3-allyl-2-[(5-cyanopyrid-2-yl)aminothiocarbonyl]acrylonitrile;
- Compound 110: 3-hydroxy-3-isopropyl-2-[(5-cyanopyrid-2-yl)aminothiocarbonyl]acrylonitrile; and
- Compound 111: 3-hydroxy-3-(propen-2-yl)-2-[(5-cyanopyrid-2-yl)aminothiocarbonyl]acrylonitrile.

EXAMPLE 39

Analytical Data

Analytical data was obtained for representative compounds using standard techniques The data is shown is Table IV.

TABLE IV

| Compound # | Appearance | MP (°C.) | NMR(360MHZ, DMSO-d$_6$) |
|---|---|---|---|
| AA12 | yellow solid | 197 | δ2.5(3H, s); 7.6(2H, d); 7.8(1H, s); 8.1(2H, d); 14.2(1H, s) |
| AA14 | white solid | | δ2.3(3H, s); 7.6(2H, d); 7.7(2H, d) |
| 3 | brown solid | 120.6d | δ0.6–0.9(4H, m); 2.2 (1H, m); 7.6(2H, d); 8.1 (2H, d); 14.4(1H, s) |
| AA10 | yellow solid | 108.5 | δ2.7(3H, s); 7.8(2H, d); 8.0(2H, d); 8.9(1H, s); 11.8(1H, s) |
| 6 | red oil | | δ1.6(3H, s); 5.6(1H, s); 6.0(1H, s); 7.6(2H, d); 8.1(2H, d); 12.3 (1H, s); 14.4(1H, s) |
| 7 | white solid | 151.6 | δ2.1(3H, s); 6.5–8.0 (1H, br s); 7.2(1H, m) 7.5(1H, m); 8.1(1H, m); 13.5(1H, s) |
| 12 | white solid | 157.4 | δ2.1(3H, s); 7.3(1H, m); 7.7(1H, m); 7.9(1H, m); 8.0(1H, br s); 13.6 (1H, s) |
| 17 | white solid | 139.6 | δ2.1(3H, s); 6.2–7.0 (1H, br s); 7.4(1H, m); 7.5(1H, m); 7.8(1H, m); 8.6(1H, s); 14.2(1H, s) |
| 27 | white solid | 216.2 | δ2.1(3H, s); 7.2(1H, s); 7.7(2H, d); 8.0(2H, d) |
| 32 | yellow solid | 255.4d | δ2.1(3H, s); 7.3(2H, m); 8.5(1H, m); 14.0 (1H, s) |
| 37 | off-white solid | 250.8d | δ2.1(3H, s); 7.4(1H, br s); 7.5(2H, m); 8.5 (1H, s); 14.2(1H, s) |
| 42 | yellow solid | 142.8d | δ2.1(3H, s); 7.1(1H, m); 7.5(1H, d); 7.7(1H, br s); 9.0(1H., d); 14.2 (1H, s) | d = decomposition

Other embodiments are within the following claims. Thus while several embodiments have been shown and described, various modifications may be made, without departing from the spirit and scope of the present invention.

I claim:

1. A compound which has the chemical formula:

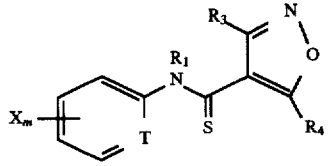

wherein T is carbon or nitrogen;
if T is carbon m is either 1, 2, 3, 4 or 5; and if T is nitrogen m is either 0, 1, 2, 3, or 4;

each X is independently selected from the group consisting of: SH, OH, lower alkyl, lower alkenyl, lower alkoxy, haloalkoxy, halogen, haloalkyl, cyano, sulfonyl-aryl, amino, aminosulfonyl, and NO$_2$;

R$_1$ is hydrogen or lower alkyl;

R$_3$ is selected from the group consisting of: hydrogen, carboxy, alkoxy, and carbalkoxy;

R$_4$ is selected from the group consisting of: alkyl, alkenyl, alkyl-aryl, alkenyl-aryl, and alkynyl-aryl; and pharmaceutically acceptable salts thereof.

2. The compound of claim 1, wherein m is either 1, 2, 3 or 4;

each X is independently selected from the group consisting of: SH, OH, lower alkyl, lower alkenyl, lower alkoxy, haloalkoxy, halogen, haloalkyl, cyano, piperidine-1-sulfonyl, amino, aminosulfonyl, and NO$_2$;

R$_1$ is hydrogen;

R$_3$ is selected from the group consisting of hydrogen, carboxy, lower alkoxy, and carbalkoxy R$_4$ is selected from the group consisting of: lower alkyl and lower alkenyl; and pharmaceutically acceptable salts thereof.

3. The compound of claim 2, wherein T is carbon;

each X is independently selected from the group consisting of: halogen, lower haloalkyl, lower haloalkoxy, piperidine-1-sulfonyl, aminosulfonyl, and cyano; R$_3$ is hydrogen; and m is either 1, 2, or 3, provided that an X is present in the para position.

4. The compound of claim 1, wherein said compound is 5-methyl-4-(4-trifluoromethylphenyl) aminothiocarbonylisoxazole or a pharmaceutically acceptable salt thereof.

5. A method of inhibiting growth of cells having hyperproliferative cell growth comprising the step of exposing said cells to a growth inhibiting amount of a compound having the chemical formula:

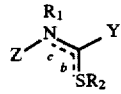

wherein R$_1$ is either hydrogen, alkyl, alkenyl, alkynyl, aryl, or is not present;

R$_2$ is either hydrogen, aryl, alkyl, alkenyl, alkynyl, or is not present;

Y is an optionally substituted isoxazolyl;

Z is selected from the group consisting of: aryl, alkyl-aryl, alkenyl-aryl, and alkynyl-aryl;

b is an optional additional bond;

c is an optional additional bond;

provided that either b or c is present as an additional bond and if b is present as the additional bond R$_2$ is not present and c is not present, and if c is present as the additional bond R$_1$ is not present and b is not present; and pharmaceutically acceptable salts thereof.

6. A method of inhibiting growth of cells having hyperproliferative cell growth comprising the step of exposing said cells to a growth inhibiting amount of a compound which has the chemical formula:

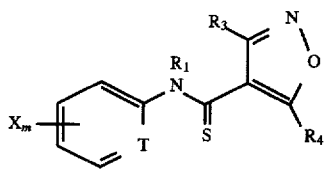

wherein T is carbon or nitrogen;

if T is carbon m is either 0, 1, 2, 3, 4 or 5; and if T is nitrogen m is either 0, 1, 2, 3, or 4;

each X is independently selected from the group consisting of: SH, OH, lower alkyl, lower alkenyl, lower alkoxy, haloalkoxy, halogen, haloalkyl, cyano, sulfonyl-aryl, amino, aminosulfonyl, and $NO_2$;

$R_1$ is hydrogen or lower alkyl;

$R_3$ is selected from the group consisting of: hydrogen, carboxy, alkoxy, and carbalkoxy;

$R_4$ is selected from the group consisting of: alkyl, alkenyl, alkyl-aryl, alkenyl-aryl, and alkynyl-aryl; and pharmaceutically acceptable salts thereof.

7. A method of treating a human patient suffering from a hyper-proliferative cell disorder comprising the step of administering to said patient a therapeutically effective amount of a pharmaceutical composition comprising a compound having the chemical formula:

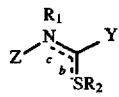

wherein $R_1$ is either hydrogen, alkyl, alkenyl, alkynyl, aryl, or is not present;

$R_2$ is either hydrogen, aryl, alkyl, alkenyl, alkynyl, or is not present;

Y is an optionally substituted isoxazolyl;

Z is selected from the group consisting of: aryl, alkyl-aryl, alkenyl-aryl, and alkynyl-aryl;

b is an optional additional bond;

c is an optional additional bond;

provided that either b or c is present as an additional bond and if b is present as the additional bond $R_2$ is not present and c is not present, and if c is present as the additional bond $R_1$ is not present and b is not present; and pharmaceutically acceptable salts thereof.

8. A method of treating a patient suffering from a hyper-proliferative cell disorder comprising the step of administering to said patient a therapeutically effective amount of a compound which has the chemical formula:

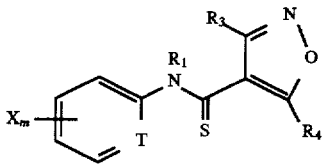

wherein T is carbon or nitrogen;

if T is carbon m is either 0, 1, 2, 3, 4 or 5; and if T is nitrogen m is either 0, 1, 2, 3, or 4;

each X is independently selected from the group consisting of: SH, OH, lower alkyl, lower alkenyl, lower alkoxy, haloalkoxy, halogen, haloalkyl, cyano, sulfonyl-aryl, amino, aminosulfonyl, and $NO_2$;

$R_1$ is hydrogen or lower alkyl;

$R_3$ is selected from the group consisting of: hydrogen, carboxy, alkoxy, and carbalkoxy;

$R_4$ is selected from the group consisting of: alkyl, alkenyl, alkyl-aryl, alkenyl-aryl, and alkynyl-aryl; and pharmaceutically acceptable salts thereof.

9. The method of claim 8, wherein said disorder is a cancer selected from the group consisting of intra-axial brain cancer, ovarian cancer, colon cancer, prostate cancer, lung cancer, Kaposi's sarcoma, and melanoma.

10. The method of claim 9, wherein said cancer is glioma.

11. The method of claim 8, wherein said disorder is either a blood vessel proliferation disorder or a fibrotic disorder.

12. The method of claim 11, wherein said blood vessel proliferative disorder is either restenosis or atherosclerosis.

13. The method of claim 8, wherein said disorder is host versus-graft-rejection.

14. A pharmaceutical composition comprising a pharmaceutically acceptable carrier and a therapeutically effective amount of the compound of any one of claims 1–4.

15. The method of claim 5, wherein said $R_1$, if present, is selected from the group consisting of:
hydrogen,
lower alkyl,
lower alkenyl,
lower alkynyl, and
optionally substituted aryl optionally containing up to five substituents each independently selected from the group consisting of: lower alkoxy, haloalkoxy, haloalkyl, aminosulfonyl, halogen, trihalomethyl, SH, OH, $NO_2$, cyano, lower alkyl, lower alkenyl, lower alkynyl, amino, carboxy, and carbalkoxy;

said $R_2$, if present, is selected from the group consisting of:
lower alkyl,
lower alkenyl,
lower alkynyl, and
optionally substituted aryl optionally containing up to five substituents each independently selected from the group consisting of: lower alkoxy, haloalkoxy, haloalkyl, aminosulfonyl, halogen, trihalomethyl, SH, OH, $NO_2$, cyano, lower alkyl, lower alkenyl, lower alkynyl, amino, carboxy, and carbalkoxy;

said Z is selected from the group consisting of: optionally substituted aryl optionally containing up to five substituents each independently selected from the group consisting of: lower alkoxy, haloalkoxy, haloalkyl, aminosulfonyl, halogen, trihalomethyl, SH, OH, $NO_2$, cyano, lower alkyl, lower alkenyl, lower alkynyl, amino, carboxy, and carbalkoxy;

lower alkyl-optionally substituted aryl optionally containing up to five substituents each independently selected from the group consisting of: lower alkoxy, haloalkoxy, haloalkyl, aminosulfonyl, halogen, trihalomethyl, SH, OH, $NO_2$, cyano, lower alkyl, lower alkenyl, lower alkynyl, amino, carboxy, and carbalkoxy;

lower alkenyl-optionally substituted aryl optionally containing up to five substituents each independently selected from the group consisting of: lower alkoxy, haloalkoxy, haloalkyl, aminosulfonyl, halogen, trihalomethyl, SH, OH, $NO_2$, cyano, lower alkyl, lower alkenyl lower alkynyl, amino, carboxy, and carbalkoxy; and lower alkynyl-optionally substituted aryl optionally containing up to five substituents each independently selected from the group consisting of: lower alkoxy, haloalkoxy, haloalkyl, aminosulfonyl, halogen, trihalomethyl, SH, OH, NO$_2$, cyano, lower alkyl, lower alkenyl, lower alkynyl, amino, carboxy, and carbalkoxy.

16. The method of claim 15, wherein said R$_1$ is hydrogen, said R$_2$ is not present, said Z is an optionally substituted phenyl optionally containing up to five substituents each independently selected from the group consisting of: lower alkoxy, haloalkoxy, haloalkyl, aminosulfonyl, halogen, trihalomethyl, SH, OH, NO$_2$, cyano, lower alkyl, lower alkenyl, lower alkynyl, amino, carboxy, and carbalkoxy; and said b is present, as the additional bond.

17. The method of claim 16, wherein said Y is optionally substituted isoxazolyl optionally containing up to two substituents each independently selected from the group consisting of: lower alkoxy, haloalkoxy, haloalkyl, aminosulfonyl, halogen, trihalomethyl, SH, OH, NO$_2$, cyano, lower alkyl, lower alkenyl, lower alkynyl, amino, carboxy, and carbalkoxy.

18. The method of claim 7, wherein said R$_1$, if present, is selected from the group consisting of:
  hydrogen,
  lower alkyl,
  lower alkenyl,
  lower alkynyl, and
  optionally substituted aryl optionally containing up to five substituents each independently selected from the group consisting of: lower alkoxy, haloalkoxy, haloalkyl, aminosulfonyl, halogen, trihalomethyl, SH, OH, NO$_2$, cyano, lower alkyl, lower alkenyl, lower alkynyl, amino, carboxy, and carbalkoxy;

said R$_2$, if present, is selected from the group consisting of:
  lower alkyl,
  lower alkenyl,
  lower alkynyl, and
  optionally substituted aryl optionally containing up to five substituents each independently selected from the group consisting of: lower alkoxy, haloalkoxy, haloalkyl, aminosulfonyl, halogen, trihalomethyl, SH, OH, NO$_2$, cyano, lower alkyl, lower alkenyl, lower alkynyl, amino, carboxy, and carbalkoxy;

said Z is selected from the group consisting of:
  optionally substituted aryl optionally containing up to five substituents each independently selected from the group consisting of: lower alkoxy, haloalkoxy, haloalkyl, aminosulfonyl, halogen, trihalomethyl, SH, OH, NO$_2$, cyano, lower alkyl, lower alkenyl, lower alkynyl, amino, carboxy, and carbalkoxy;
  lower alkyl-optionally substituted aryl optionally containing up to five substituents each independently selected from the group consisting of: lower alkoxy, haloalkoxy, haloalkyl, aminosulfonyl, halogen, trihalomethyl, SH, OH, NO$_2$, cyano, lower alkyl, lower alkenyl, lower alkynyl, amino, carboxy, and carbalkoxy;
  lower alkenyl-optionally substituted aryl optionally containing up to five substituents each independently selected from the group consisting of: lower alkoxy, haloalkoxy, haloalkyl, aminosulfonyl, halogen, trihalomethyl, SH, OH, NO$_2$, cyano, lower alkyl, lower alkenyl, lower alkynyl, amino, carboxy, and carbalkoxy; and
  lower alkynyl-optionally substituted aryl optionally containing up to five substituents each independently selected from the group consisting of: lower alkoxy, haloalkoxy, haloalkyl, aminosulfonyl, halogen, trihalomethyl, SH, OH, NO$_2$, cyano, lower alkyl, lower alkenyl, lower alkynyl, amino, carboxy, and carbalkoxy.

19. The method of claim 18, wherein said R$_1$ is hydrogen, said R$_2$ is not present, said Z is an optionally substituted phenyl optionally containing up to five substituents each independently selected from the group consisting of: lower alkoxy, haloalkoxy, haloalkyl, aminosulfonyl, halogen, trihalomethyl, SH, OH, NO$_2$, cyano, lower alkyl, lower alkenyl, lower alkynyl, amino, carboxy, and carbalkoxy; and said b is present as the additional bond.

20. The method of claim 19, wherein said Y is optionally substituted isoxazolyl optionally containing up to two substituents each independently selected from the group consisting of: lower alkoxy, haloalkoxy, haloalkyl, aminosulfonyl, halogen, trihalomethyl, SH, OH, NO$_2$, cyano, lower alkyl, lower alkenyl, lower alkynyl, amino, carboxy, and carbalkoxy.

21. The method claim 8, wherein said compound is 5-methyl-4-(4-trifluoromethylphenyl) aminothiocarbonylisoxazole, or a pharmaceutically acceptable salt thereof.

22. The method claim 8, wherein m is either 1, 2, 3 or 4;

each X is independently selected from the group consisting of: SH, OH, lower alkyl, lower alkenyl, lower alkoxy, haloalkoxy, halogen, haloalkyl, cyano, piperidine-1-sulfonyl, amino, aminosulfonyl, and NO$_2$;

R$_1$ is hydrogen;

R$_3$ is selected from the group consisting of hydrogen, carboxy, lower alkoxy, and carbalkoxy;

R$_4$ is selected from the group consisting of: lower alkyl and lower alkenyl; and pharmaceutically acceptable salts thereof.

23. The method claim 22, wherein T is carbon;

each X is independently selected from the group consisting of: halogen, lower haloalkyl, lower haloalkoxy, piperidine-1-sulfonyl, aminosulfonyl, and cyano;

R$_3$ is hydrogen; and m is either 1, 2, or 3, provided that an X is present in the para position.

24. The method of any one of claims 18–19 20, or 21–23, wherein said disorder is a cancer selected from the group consisting of intra-axial brain cancer, ovarian cancer, colon cancer, prostate cancer, lung cancer, Kaposi's sarcoma, and melanoma.

25. The method of claim 24, wherein said cancer is glioma.

26. The method of any one of claims 18–19, 20, or 21–23, wherein said disorder is either a blood vessel proliferation disorder or a fibrotic disorder.

27. The method of claim 26, wherein said disorder is atherosclerosis.

28. A pharmaceutical composition comprising a pharmaceutically acceptable carrier and a therapeutically effective amount of a compound which has the chemical formula:

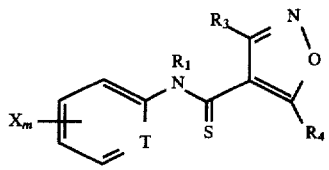

wherein T is carbon or nitrogen;

if T is carbon m is either 0, 1, 2, 3, 4 or 5; and if T is nitrogen m is either 0, 1, 2, 3, or 4;

each X is independently selected from the group consisting of: SH, OH, lower alkyl, lower alkenyl, lower alkoxy, haloalkoxy, halogen, haloalkyl, cyano, sulfonyl-aryl, amino, aminosulfonyl, and $NO_2$;

$R_1$ is hydrogen or lower alkyl;

$R_3$ is selected from the group consisting of: hydrogen, carboxy, alkoxy, and carbalkoxy;

$R_4$ is selected from the group consisting of: alkyl, alkenyl, alkyl-aryl, alkenyl-aryl, and alkynyl-aryl; and pharmaceutically acceptable salts thereof.

* * * * *